United States Patent
Bhatia et al.

(10) Patent No.: US 10,883,998 B2
(45) Date of Patent: Jan. 5, 2021

(54) METHODS AND PRODUCTS FOR IN VIVO ENZYME PROFILING

(71) Applicant: Massachusetts Institute of Technology, Cambridge, MA (US)

(72) Inventors: Sangeeta N. Bhatia, Lexington, MA (US); Geoffrey A. von Maltzahn, Boston, MA (US); Gabriel A. Kwong, Atlanta, GA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/966,385

(22) Filed: Apr. 30, 2018

(65) Prior Publication Data

US 2018/0328941 A1    Nov. 15, 2018

Related U.S. Application Data

(60) Division of application No. 14/166,481, filed on Jan. 28, 2014, now Pat. No. 9,970,941, which is a continuation of application No. 12/715,965, filed on Mar. 2, 2010, now Pat. No. 8,673,267.

(60) Provisional application No. 61/156,660, filed on Mar. 2, 2009.

(51) Int. Cl.
*G01N 33/68* (2006.01)
*C07K 7/06* (2006.01)
*C12Q 1/37* (2006.01)
*C12Q 1/56* (2006.01)

(52) U.S. Cl.
CPC .......... *G01N 33/6848* (2013.01); *C07K 7/06* (2013.01); *C12Q 1/37* (2013.01); *C12Q 1/56* (2013.01); *G01N 33/6842* (2013.01)

(58) Field of Classification Search
None
See application file for complete search history.

(56) References Cited

U.S. PATENT DOCUMENTS

| | | | |
|---|---|---|---|
| 5,500,161 A | 3/1996 | Andrianov et al. |
| 5,811,252 A | 9/1998 | Verheijen |
| 5,885,775 A | 3/1999 | Haff et al. |
| 6,312,390 B1 | 11/2001 | Phillips |
| 6,592,847 B1 | 7/2003 | Weissleder et al. |
| 6,597,996 B1 | 7/2003 | Venkataraman et al. |
| 6,629,040 B1 | 9/2003 | Goodlett et al. |
| 6,824,981 B2 | 11/2004 | Chait et al. |
| 7,041,453 B2 | 5/2006 | Yang |
| 7,179,655 B2 | 2/2007 | Patricelli |
| 7,329,506 B2 | 2/2008 | William |
| 7,412,332 B1 | 8/2008 | Venkataraman et al. |
| 7,456,269 B2 | 11/2008 | Gurney et al. |
| 7,468,258 B2 | 12/2008 | Owen |
| 7,544,518 B2 | 6/2009 | Aebersold et al. |
| 7,595,155 B2 | 9/2009 | Murakami |
| 7,879,574 B2 | 2/2011 | Packard et al. |
| 7,985,401 B2 | 7/2011 | Jiang et al. |
| 8,673,267 B2 | 3/2014 | Bhatia et al. |
| 8,841,085 B2 | 9/2014 | Kwon et al. |
| 8,969,027 B2 | 3/2015 | Bossmann et al. |
| 9,006,415 B2 | 4/2015 | Ren et al. |
| 9,072,792 B2 | 7/2015 | Jiang et al. |
| 9,657,326 B2 | 5/2017 | Ruether et al. |
| 9,695,251 B2 | 7/2017 | Tsien et al. |
| 9,808,532 B2 | 11/2017 | Tsien et al. |
| 9,970,941 B2 | 5/2018 | Bhatia et al. |
| 10,006,916 B2 | 6/2018 | Kwong et al. |
| 10,527,619 B2 | 1/2020 | Bhatia et al. |
| 2002/0119490 A1 | 8/2002 | Aebersold et al. |
| 2004/0091943 A1 | 5/2004 | Schneider |
| 2005/0107583 A1 | 5/2005 | Jiang et al. |
| 2005/0260695 A1 | 11/2005 | Fleming et al. |
| 2006/0008856 A1 | 1/2006 | Singh et al. |
| 2006/0292631 A1 | 12/2006 | Broberg et al. |
| 2007/0010433 A1 | 1/2007 | Albrechtsen et al. |
| 2007/0048752 A1 | 3/2007 | Yan et al. |
| 2007/0207555 A1 | 9/2007 | Guerra et al. |
| 2008/0026480 A1 | 1/2008 | Guerra |
| 2008/0064607 A1 | 3/2008 | Yang |
| 2008/0095758 A1 | 4/2008 | Lee et al. |
| 2008/0113875 A1 | 5/2008 | Chaurand et al. |
| 2008/0213377 A1 | 9/2008 | Bhatia et al. |
| 2008/0226562 A1* | 9/2008 | Groves ............. A61K 49/0002 424/9.6 |
| 2008/0241955 A1 | 10/2008 | Purkayastha et al. |
| 2009/0016988 A1 | 1/2009 | Buckley |
| 2009/0088332 A1 | 4/2009 | Ju et al. |
| 2009/0156424 A1 | 6/2009 | Thompson |
| 2009/0230300 A1 | 9/2009 | Trevejo et al. |
| 2009/0246142 A1 | 10/2009 | Bhatia et al. |

(Continued)

FOREIGN PATENT DOCUMENTS

AU    2017104157    8/2019
CN    102558362 A    7/2012

(Continued)

OTHER PUBLICATIONS

Böhm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.

(Continued)

*Primary Examiner* — Anand U Desai
(74) *Attorney, Agent, or Firm* — Wolf, Greenfield & Sacks, P.C.

(57) ABSTRACT

The present invention relates to methods and products associated with in vivo enzyme profiling. In particular, the invention relates to methods of in vivo processing of exogenous molecules followed by detection of signature molecules as representative of the presence of active enzymes associated with diseases or conditions. The invention also relates to products, kits, and databases for use in the methods of the invention.

30 Claims, 13 Drawing Sheets
Specification includes a Sequence Listing.

(56) References Cited

U.S. PATENT DOCUMENTS

| | | |
|---|---|---|
| 2010/0022408 A1 | 1/2010 | Singh et al. |
| 2010/0124757 A1 | 5/2010 | Kwon et al. |
| 2010/0190193 A1 | 7/2010 | Calatzis et al. |
| 2010/0240050 A1 | 9/2010 | Bhatia et al. |
| 2010/0317542 A1 | 12/2010 | Lim et al. |
| 2013/0078188 A1 | 3/2013 | Tsien et al. |
| 2013/0295129 A1 | 11/2013 | Irvine et al. |
| 2013/0315906 A1 | 11/2013 | Lowman et al. |
| 2014/0234431 A1 | 8/2014 | Bhatia et al. |
| 2014/0255313 A1 | 9/2014 | Vasiljeva et al. |
| 2014/0303014 A1 | 10/2014 | Kwong et al. |
| 2014/0363833 A1 | 12/2014 | Bhatia et al. |
| 2014/0364368 A1 | 12/2014 | Lin et al. |
| 2015/0165062 A1 | 6/2015 | Liao et al. |
| 2016/0289324 A1 | 10/2016 | Moore et al. |
| 2017/0305968 A1 | 10/2017 | Tsien et al. |
| 2018/0196058 A1 | 7/2018 | Kwong et al. |
| 2018/0335429 A1* | 11/2018 | Bhatia .................. G01N 33/553 |
| 2019/0128873 A1 | 5/2019 | Bhatia et al. |
| 2019/0144917 A1 | 5/2019 | Bhatia et al. |
| 2019/0212291 A1 | 7/2019 | Dudani et al. |
| 2019/0271704 A1 | 9/2019 | Bhatia et al. |
| 2020/0096514 A1 | 3/2020 | Bhatia et al. |

FOREIGN PATENT DOCUMENTS

| | | |
|---|---|---|
| CN | 103012595 A | 4/2013 |
| CN | 108484847 A | 9/2018 |
| EP | 2686000 | 1/2014 |
| JP | 2004-506900 | 3/2004 |
| JP | 2004-129651 | 4/2004 |
| JP | 2007-24631 A2 | 2/2007 |
| JP | 2007-206054 A | 8/2007 |
| JP | 2009-108037 | 5/2009 |
| JP | 2009-524688 | 7/2009 |
| JP | 2009-538430 A | 11/2009 |
| JP | 2013-060452 | 4/2013 |
| WO | WO 2002/014867 A2 | 2/2002 |
| WO | WO 2006/034370 A2 | 3/2006 |
| WO | WO 2007/060921 A1 | 5/2007 |
| WO | WO 2008/072676 A1 | 6/2008 |
| WO | WO 2008/093513 A1 | 8/2008 |
| WO | WO 2008/127019 A1 | 10/2008 |
| WO | WO 2010/101628 A2 | 9/2010 |
| WO | WO 2011/008996 A2 | 1/2011 |
| WO | WO 2012/085080 A1 | 6/2012 |
| WO | WO 2012/125808 A1 | 9/2012 |
| WO | WO 2014/107599 A2 | 7/2014 |
| WO | WO 2014/197816 | 12/2014 |
| WO | WO 2014/197840 A1 | 12/2014 |

OTHER PUBLICATIONS

Dennis et al., Albumin binding as a general strategy for improving the pharmacokinetics of proteins. J Biol Chem. Sep. 20, 2002;277(38):35035-43. Epub Jul. 15, 2002.

Deshpande et al., Current trends in the use of liposomes for tumor targeting. Nanomedicine (Lond). Sep. 2013;8(9):1509-28. doi:10.2217/nnm.13.118.

Dudani et al., Classification of prostate cancer using a protease activity nanosensor library. Proc Natl Acad Sci U S A. Sep. 4, 2018;115(36):8954-8959. doi: 10.1073/pnas.1805337115. Epub Aug. 20, 2018.

Dudani et al., Harnessing Protease Activity to Improve Cancer Care. Ann Rev Cancer Biol. Mar. 2018;2:353-376.

Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.

Dudani et al., Sustained-release synthetic biomarkers for monitoring thrombosis and inflammation using point-of-care compatible readouts. Adv Funct Mater. May 3, 2016;26(17):2919-2928. doi: 10.1002/adfm.201505142. Epub Mar. 22, 2016.

Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015;12(1). doi:10.1038/nrclinonc.2014.70.

Kaminskas et al., Methotrexate-conjugated PEGylated dendrimers show differential patterns of deposition and activity in tumor-burdened lymph nodes after intravenous and subcutaneous administration in rats. Mol Pharm. Feb. 2015;12(2):432-43. doi: 10.1021/mp500531e. Epub Jan. 20, 2015.

Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.

Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.

Lebeau et al., Imaging active urokinase plasminogen activator in prostate cancer. Cancer Res. Apr. 1, 2015;75(7):1225-35. doi:10.1158/0008-5472.CAN-14-2185. Epub Feb. 11, 2015.

McLennan et al., Subcutaneous drug delivery and the role of the lymphatics. Drug Discov Today Technol. 2005 Spring;2(1):89-96. doi:10.1016/j.ddtec.2005.05.006.

Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.

Prensner et al., Beyond PSA: the next generation of prostate cancer biomarkers. Sci Transl Med. Mar. 28, 2012;4(127):127rv3. doi:10.1126/scitranslmed.3003180.

Sawyers, The cancer biomarker problem. Nature. Apr. 3, 2008;452(7187):548-52. doi: 10.1038/nature06913.

Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.

Sugahara et al., Coadministration of a tumor-penetrating peptide enhances the efficacy of cancer drugs. Science. May 21, 2010;328(5981):1031-5. doi:10.1126/science.1183057. Epub Apr. 8, 2010.

Sutherland et al., RGD-Binding Integrins in Prostate Cancer: Expression Patterns and Therapeutic Prospects against Bone Metastasis. Cancers (Basel). Oct. 26, 2012;4(4):1106-45. doi:10.3390/cancers4041106.

Taylor et al., Integrative genomic profiling of human prostate cancer. Cancer Cell. Jul. 13, 2010;18(1):11-22. doi:10.1016/j.ccr.2010.05.026. Epub Jun. 24, 2010.

Thorek et al., Internalization of secreted antigen-targeted antibodies by the neonatal Fc receptor for precision imaging of the androgen receptor axis. Sci Transl Med. Nov. 30, 2016;8(367):367ra167.

Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.

Withana et al., Labeling of active proteases in fresh-frozen tissues by topical application of quenched activity-based probes. Nat Protoc. Jan. 2016;11(1):184-91. doi: 10.1038/nprot.2016.004. Epub Dec. 30, 2015.

Xia et al., Multiplex detection of protease activity with quantum dot nanosenors prepared by Intein-Mediated specific bioconjugation. Analytical Chemistry. Nov. 15, 2008; 22(80) 8649-8655.

Abudayyeh, Nanoparticle-Chaperoned Urinary "Synthetic Biomarkers" for Profiling Proteases in Cancer. Thesis. Department of Mechanical Engineering. Jun. 2012.

Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.

Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.

Asai et al., A colorimetric assay for plasma antithrombin III using a new synthetic peptide substrate (PS-915). Clin Chim Acta. Dec. 29, 1984;144(2-3):163-71.

(56) References Cited

OTHER PUBLICATIONS

Baruch et al., Enzyme activity—it's all about image. Trends Cell Biol. Jan. 2004;14(1):29-35.
Becker et al., Thrombin: Structure, Biochemistry, Measurement, and Status in Clinical Medicine. J Thromb Thrombolysis. Jul. 1998;5(3):215-229.
Blum et al., Noninvasive optical imaging of cysteine protease activity using fluorescently quenched activity-based probes. Nat Chem Biol. Oct. 2007;3(10):668-77. Epub Sep. 9, 2007.
Bounameaux et al., Plasma measurement of D-dimer as diagnostic aid in suspected venous thromboembolism: an overview. Thromb Haemost. Jan. 1994;71(1):1-6.
Chen et al., A unique substrate recognition profile for matrix metalloproteinase-2. J Biol Chem. Feb. 8, 2002;277(6):4485-91.
Daniel et al., Implantable diagnostic device for cancer monitoring. Biosens Bioelectron. Jul. 15, 2009;24(11):3252-7. Epub Apr. 16, 2009.
De La Rica et al., Enzyme-responsive nanoparticles for drug release and diagnostics. Adv Drug Deliv Rev. Aug. 2012;64(11):967-78. doi: 10.1016/j.addr.2012.01.002. Epub Jan. 14, 2012.
Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05.018. Epub May 25, 2013.
Dranoff, Cytokines in cancer pathogenesis and cancer therapy. Nat Rev Cancer. Jan. 2004;4(1):11-22.
D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.
Farrell et al., Non-motor parkinsonian pathology in aging A53T α-synuclein mice is associated with progressive synucleinopathy and altered enzymatic function. J Neurochem. Feb. 2014;128(4):536-46. doi: 10.1111/jnc.12481. Epub Nov. 20, 2013.
Fowlkes et al., Proteolysis of insulin-like growth factor binding protein-3 during rat pregnancy: a role for matrix metalloproteinases. Endocrinology. Dec. 1994;135(6):2810-3.
Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.
Genbank Submission; NIH/NCBI, Accession No. 2WV1_A; Kovalevskiy et al.; Mar. 24, 2010.
Genbank Submission; NIH/NCBI, Accession No. CAG01641; Mar. 17, 2004.
Genbank Submission; NIH/NCBI, Accession No. NP.sub.--938673; Cerdeno-Tarraga et al.; Jun. 3, 2010.
Genbank Submission; NIH/NCBI, Accession No. NP_731669; Hoskins et al.; Dec. 18, 2009.
Genbank Submission; NIH/NCBI, Accession No. XP.sub.--001385378; Jeffries et al.; Apr. 11, 2008.
Genbank Submission; NIH/NCBI, Accession No. XP.sub.--002097000; Clark et al.; Aug. 12, 2009.
Genbank Submission; NIH/NCBI, Accession No. XP.sub.--00234527.; Jul. 7, 2006.
Genbank Submission; NIH/NCBI, Accession No. ZP.sub.--03507634; Gonzalez et al.; Dec. 19, 2008.
Genbank Submission; NIH/NCBI, Accession No. ZP.sub.--06431346; Small et al.; Jun. 9, 2010.
Ghadiali, James E. et al., "Enzyme-Responsive Nanoparticle Systems," Advanced Materials, vol. 20(22):4359-4363 (2008).
Giljohann, et al., Drivers of biodiagnostic development. Nature. Nov. 26, 2009;462(7272):461-4. doi: 10.1038/nature08605.
Ginsberg et al., Sensitivity and specificity of a rapid whole-blood assay for D-dimer in the diagnosis of pulmonary embolism. Ann Intern Med. Dec. 15, 1998;129(12):1006-11.
Grayson et al., Multi-pulse drug delivery from a resorbable polymeric microchip device. Nat Mater. Nov. 2003;2(11):767-72.
Gross, Mass Spectrometry: A Textbook. Springer. $2^{nd}$ ed. Mar. 1, 2011. Chapter 9. 415-452.

Haro et al., Matrix metalloproteinase-7-dependent release of tumor necrosis factor-alpha in a model of herniated disc resorption. J Clin Invest. Jan. 2000;105(2):143-50.
Haun et al., Micro-NMR for rapid molecular analysis of human tumor samples. Sci Transl Med. Feb. 23, 2011;3(71):71ra16. doi: 10.1126/scitranslmed.3002048.
Imai et al., Degradation of decorin by matrix metalloproteinases: identification of the cleavage sites, kinetic analyses and transforming growth factor-beta1 release. Biochem J. Mar. 15, 1997;322 (Pt 3):809-14.
Ito et al., Degradation of interleukin 1beta by matrix metalloproteinases. J Biol Chem. Jun. 21, 1996;271(25):14657-60.
Jaffer et al., In vivo imaging of thrombin activity in experimental thrombi with thrombin-sensitive near-infrared molecular probe. Arterioscler Thromb Vasc Biol. Nov. 1, 2002;22(11):1929-35.
Johnson et al., Computer program (SEQPEP) to aid in the interpretation of high-energy collision tandem mass spectra of peptides. Biomed Environ Mass Spectrom. Nov. 1989;18(11):945-57.
Kastelic et al., Stefin B, the major low molecular weight inhibitor in ovarian carcinoma. Cancer Lett. Jul. 15, 1994;82(1):81-8.
Kircher et al., A dual fluorochrome probe for imaging proteases. Bioconjug Chem. Mar.-Apr. 2004;15(2):242-8.
Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.
Kwon et al., Ultrasensitive tumour-penetrating nanosensors of protease activity. Nat Biomed Eng. 2017;1. pii: 0054. doi:10.1038/s41551-017-0054. Epub Apr. 10, 2017.
Kwong et al., Mass-encoded synthetic biomarkers for multiplexed urinary monitoring of disease. Nat Biotechnol. Jan. 2013;31(1):63-70. doi: 10.1038/nbt.2464. Epub Dec. 16, 2012.
Kwong et al., Mathematical framework for activity-based cancer biomarkers. Proc Natl Acad Sci U S A. Oct. 13, 2015;112(41):12627-32. doi: 10.1073/pnas.1506925112. Epub Sep. 28, 2015.
Lange et al., Selected reaction monitoring for quantitative proteomics: a tutorial. Mol Syst Biol. 2008;4:222. doi: 10.1038/msb.2008.61. Epub Oct. 14, 2008.
Larsen et al., Assay of plasma heparin using thrombin and the chromogenic substrate H-D-Phe-Pip-Arg-pNA (S-2238). Thromb Res. Aug. 1978;13(2):285-8.
Levi et al., Matrix metalloproteinase 2 releases active soluble ectodomain of fibroblast growth factor receptor 1. Proc Natl Acad Sci U S A. Jul. 9, 1996;93(14):7069-74.
Lin et al., Drug-induced amplification of nanoparticle targeting to tumors. Nano Today. Oct. 2014;9(5):550-559. doi:10.1016/j.nantod.2014.09.001. Epub Sep. 23, 2014.
Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.
Mallick et al., Computational prediction of proteotypic peptides for quantitative proteomics. Nat Biotechnol. Jan. 2007;25(1):125-31. Epub Dec. 31, 2006.
Mañes et al., The matrix metalloproteinase-9 regulates the insulin-like growth factor-triggered autocrine response in DU-145 carcinoma cells. J Biol Chem. Mar. 12, 1999;274(11):6935-45.
Martinez et al., Diagnostics for the developing world: microfluidic paper-based analytical devices. Anal Chem. Jan. 1, 2010;82(1):3-10. doi: 10.1021/ac9013989.
Mira et al., Insulin-like growth factor I-triggered cell migration and invasion are mediated by matrix metalloproteinase-9. Endocrinology. Apr. 1999;140(4):1657-64.
Mirtti et al., Expression of cystatins, high molecular weight cytokeratin, and proliferation markers in prostatic adenocarcinoma and hyperplasia. Prostate. Mar. 1, 2003;54(4):290-8.
Mitchell et al., Assay for plasma heparin using a synthetic peptide substrate for thrombin: introduction of the fluorophore aminoisophthalic acid, dimethyl ester. Thromb Res. Jul. 1978;13(1):47-52.
Morris et al., Urine and plasma levels of fibrinopeptide B in patients with deep vein thrombosis and pulmonary embolism. Thromb Res. May 1, 2003;110(2-3):159-65.
Nagase et al., Matrix metalloproteinases. J Biol Chem. Jul. 30, 1999;274(31):21491-4.

(56) References Cited

OTHER PUBLICATIONS

Nahrendorf et al., Hybrid in vivo FMT-CT imaging of protease activity in atherosclerosis with customized nanosensors. Arterioscler Thromb Vasc Biol. Oct. 2009;29(10):1444-51. doi:10.1161/ATVBAHA. 109.193086. Epub Jul. 16, 2009.
Nomura et al., Activity-based protein profiling for biochemical pathway discovery in cancer. Nat Rev Cancer. Sep. 2010;10(9):630-8. doi: 10.1038/nrc2901. Epub Aug. 12, 2010.
Olson et al., In vivo fluorescence imaging of atherosclerotic plaques with activatable cell-penetrating peptides targeting thrombin activity. Integr Biol (Camb). Jun. 2012;4(6):595-605. doi: 10.1039/c2ib00161f. Epub Apr. 26, 2012.
Park et al., Magnetic Iron Oxide Nanoworms for Tumor Targeting and Imaging. Adv Mater. May 5, 2008;20(9):1630-1635.
Park et al., Systematic surface engineering of magnetic nanoworms for in vivo tumor targeting. Small. Mar. 2009;5(6):694-700. doi: 10.1002/smll.200801789.
Peer et al., Nanocarriers as an emerging platform for cancer therapy. Nat Nanotechnol. Dec. 2007;2(12):751-60.
Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.
Posthuma-Trumpie et al., Lateral flow (immuno)assay: its strengths, weaknesses, opportunities and threats. A literature survey. Anal Bioanal Chem. Jan. 2009;393(2):569-82. doi: 10.1007/s00216-008-2287-2. Epub Aug. 13, 2008.
Powell et al., The metalloproteinase matrilysin proteolytically generates active soluble Fas ligand and potentiates epithelial cell apoptosis. Curr Biol. Dec. 16-30, 1999;9(24):1441-7.
Rajah et al., Elevated levels of the IGF-binding protein protease MMP-1 in asthmatic airway smooth muscle. Am J Respir Cell Mol Biol. Feb. 1999;20(2):199-208.
Rennke, How does glomerular epithelial cell injury contribute to progressive glomerular damage? Kidney Int Suppl. Feb. 1994;45:S58-63.
Rijkers et al., Design and synthesis of thrombin substrates with modified kinetic parameters. Thromb Res. Sep. 15, 1995;79(5-6):491-9.
Roepstorff et al., Proposal for a common nomenclature for sequence ions in mass spectra of peptides. Biomed Mass Spectrom. Nov. 1984;11(11):601.
Ross et al., Multiplexed protein quantitation in *Saccharomyces cerevisiae* using amine-reactive isobaric tagging reagents. Mol Cell Proteomics. Dec. 2004;3(12):1154-69. Epub Sep. 22, 2004.
Ruoslahti et al., Targeting of drugs and nanoparticles to tumors. J Cell Biol. Mar. 22, 2010;188(6):759-68. doi: 10.1083/jcb.200910104. Epub Mar. 15, 2010.
Santini et al., A controlled-release microchip. Nature. Jan. 28, 1999;397(6717):335-8.
Schonbeck et al., Generation of biologically active IL-1 beta by matrix metalloproteinases: a novel caspase-1-independent pathway of IL-1 beta processing. J Immunol. Oct. 1, 1998;161(7):3340-6.
Schuerle et al., Magnetically Actuated Protease Sensors for in Vivo Tumor Profiling. Nano Lett. Oct. 12, 2016;16(10):6303-6310. Epub Sep. 13, 2016.
Shariat et al., Urine detection of survivin is a sensitive marker for the noninvasive diagnosis of bladder cancer. J Urol. Feb. 2004;171(2 Pt 1):626-30.
Smith et al., Rapid identification of highly active and selective substrates for stromelysin and matrilysin using bacteriophage peptide display libraries. J Biol Chem. Mar. 24, 1995;270(12):6440-9.
Suzuki et al., Matrix metalloproteinase-3 releases active heparin-binding EGF-like growth factor by cleavage at a specific juxtamembrane site. J Biol Chem. Dec. 12, 1997;272(50):31730-7.
Tascilar et al., Role of tumor markers and mutations in cells and pancreatic juice in the diagnosis of pancreatic cancer. Ann Oncol. 1999;10 Suppl 4:107-10.
Thompson et al., Tandem mass tags: a novel quantification strategy for comparative analysis of complex protein mixtures by MS/MS.

Anal Chem. Apr. 15, 2003;75(8):1895-904. Erratum in: Anal Chem. Sep. 15, 2003;75(18):4942. Johnstone, R [added]. Anal Chem. Jun. 15, 2006;78(12):4235. Mohammed, A Karim A [added].
Tockman et al., Considerations in bringing a cancer biomarker to clinical application. Cancer Res. May 1, 1992;52(9 Suppl):2711s-2718s.
Truong et al., Isotope-coded chemical reporter and acid-cleavable affinity reagents for monitoring protein sulfenic acids. Bioorg Med Chem Lett. Sep. 1, 2011;21(17):5015-20. doi: 10.1016/j.bmcl.2011.04.115. Epub May 3, 2011.
Tung et al., A novel near-infrared fluorescence sensor for detection of thrombin activation in blood. Chembiochem. Mar. 1, 2002;3(2-3):207-11.
Warren et al., Point-of-care diagnostics for noncommunicable diseases using synthetic urinary biomarkers and paper microfluidics. Proc Natl Acad Sci U S A. Mar. 11, 2014;111(10):3671-6. doi:10.1073/pnas.1314651111. Epub Feb. 24, 2014.
Weissleder et al., In vivo imaging of tumors with protease-activated near-infrared fluorescent probes. Nat Biotechnol. Apr. 1999;17(4):375-8.
Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.
Welser et al., Protease sensing with nanoparticle based platforms. Analyst. Jan. 7, 2011;136(1):29-41. doi: 10.1039/c0an00429d. Epub Sep. 28, 2010.
Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi: 10.1074/mcp.M900254-MCP200. Epub Oct. 20, 2009.
Whiteaker et al., Antibody-based enrichment of peptides on magnetic beads for mass-spectrometry-based quantification of serum biomarkers. Anal Biochem. Mar. 1, 2007;362(1):4454. Epub Dec. 20, 2006.
Whitney et al., Ratiometric activatable cell-penetrating peptides provide rapid in vivo readout of thrombin activation. Angew Chem Int Ed Engl. Jan. 2, 2013;52(1):325-30. doi: 10.1002/anie.201205721. Epub Oct. 18, 2012.
Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.
Yager et al., Point-of-care diagnostics for global health. Annu Rev Biomed Eng. 2008;10:10744. doi: 10.1146/annurev.bioeng.10.061807.160524.
Yi et al., Cell surface-localized matrix metalloproteinase-9 proteolytically activates TGF-beta and promotes tumor invasion and angiogenesis. Genes Dev. Jan. 15, 2000;14(2):163-76.
Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.
Zieske, A perspective on the use of iTRAQ reagent technology for protein complex and profiling studies. J Exp Bot. 2006;57(7):1501-8. Epub Mar. 30, 2006.
Acharige et al., Breath-based diagnosis of fungal infections. J Breath Res. Feb. 6, 2018;12(2):027108, 7 pages. doi: 10.1088/1752-7163/aa98a1.
Amstad et al., Photo- and thermoresponsive polymersomes for triggered release. Angew Chem Int Ed. 2012;51:1-6.
Baeuchamp et al., Real-time breath gas analysis for pharmacokinetics: monitoring exhaled breath by on-line proton-transfer-reaction mass spectrometry after ingestion of eucalyptol-containing capsules. J Breath Res. Jun. 2010;4(2):026006, 13 pages. doi: 10.1088/17527155/4/2/026006. Epub Apr. 22, 2010.
Bartlett, Diagnostic tests for agents of community-acquired pneumonia. Clin Infect Dis. May 2011. 52(Suppl 4):S296-304. doi: 10.1093/cid/cir045.
Bascom et al., Use of Enzyme Tests in Characterization and Identification of Aerobic and Facultatively Anaerobic Gram-Positive Cocci. Clin Microbiol Rev. Apr. 1998; 11(2): 318-340.
Berger, Helicobacter pylori breath tests. BMJ. May 25, 2002;324:1263.

(56) References Cited

OTHER PUBLICATIONS

Bonomi et al., Detection of enzyme activity through catalytic signal amplification with functionalized gold nanoparticles. Angew Chem Int Ed. 2011;50:2307-12.

Buss et al., Protease activity sensors noninvasively classify bacterial infections and antibiotic responses. EBioMedicine. Dec. 2018;38:248-56. doi:10.1016/j.ebiom.2018.11.031.

Caliendo et al., Better Tests, Better Care: Improved Diagnostics for Infectious Diseases. Clin Infect Dis. Dec. 2013;57(3):S139-S170.

Castillo et al., Sensitive substrates for human leukocyte and porcine pancreatic elastase: A study of the merits of various chromophoric and fluorogenic leaving groups in assays for serine proteases. Anal Biochem. Oct. 1979;99(1):53-64.

Chan et al., Inhalable Nanosensors for Rapid Breath-Based Pathogen Identification in Respiratory Infection. Revolutions in Biotechnology. MIT. Presented Mar. 5-6, 2018 at Tang Center, MIT Campus. 1 page.

Cheng et al., Ultrasensitive scanometric strategy for detection of matrix metalloproteinases using a histidine tagged peptide—Au nanoparticle probe. Chem Commun. 2011;47:2877-9.

Coelho et al., Usefulness of C-reactive protein in monitoring the severe community-acquired pneumonia clinical course. Crit Care. Aug. 2007; 11(4):R92.

Cohen et al., Detection and localization of surgically resectable cancers with a multi- analyte blood test. Science. 2018;3247(80):1-10.

El Badrawy et al., Matrix Metalloproteinase-9 Expression in Lung Cancer Patients and Its Relation to Serum MMP-9 Activity, Pathologic Type, and Prognosis. J Bronchol Interven Pulmonol. Oct. 2014; 21(4):327-34. doi: 10.1097/LBR.0000000000000094.

Elegbede et al., Mechanistic studies of the triggered release of liposomal contents by matrix metalloproteinase-9. J Am Chem Soc. Aug. 13, 2008;130(32):10633-42. doi: 10.1021/ja801548g. Epub Jul. 22, 2008.

Elston et al., New continuous and specific fluorometric assays for Pseudomonas aeruginosa elastase and LasA protease. Anal Biochem. Sep. 2007;368(1):87-94.

Fernandez et al., Volatile Biomarkers in Breath Associated With Liver Cirrhosis—Comparisons of Pre- and Post-liver Transplant Breath Samples. EBIOM. 2015;2:1243-50.

Figueiredo et al., Near infrared thoracoscopy of tumoral protease activity for improved detection of peripheral lung cancer. Int J Cancer. Jun. 2006;118(11):2672-7. doi: 10.1002/ijc.21713.

Gaieska et al., Impact of time to antibiotics on survival in patients with severe sepsis or septic shock in whom early goal-directed therapy was initiated in the emergency department. Crit Care Med. Apr. 2010;38(4):1045-53. doi: 10.1097/CCM.0b013e3181cc4824.

Ghoshal et al., How to Interpret Hydrogen Breath Tests. J Neurogastroenterol Motil. 2011;17:312-7.

Haiko et al., The omptins of Yersinia pestis and *Salmonella enterica* cleave the reactive center loop of plasminogen activator inhibitor 1. J Bacteriol. Sep. 2010;192(18):4553-61. doi: 10.1128/Jb.00458-10. Epub Jul. 16, 2010.

Haskins, The application of stable isotopes in biomedical research. Biomed Mass Spectrom. Jul. 1982;9(7):269-77.

Heaney et al., Real-time monitoring of exhaled volatiles using atmospheric pressure chemical ionization on a compact mass spectrometer. Bioanalysis. Jul. 2016;8(13):1325-36. doi: 10.4155/bio-2016-0045. Epub Jun. 9, 2016.

Herbig et al., Towards standardization in the analysis of breath gas volatiles. J Breath Res. 2014;8:1-11.

Holliday et al., Rapid Identification of *Staphylococcus aureus* by Using Fluorescent Staphylocoagulase Assays. J Clin Microbiol. Apr. 1999;37(4):1190-2.

Iwasaki et al., Control of adaptive immunity by the innate immune system. Nat Immunol. Mar. 19, 2015;16(4):343-53.

Janzen et al., Colorimetric sensor arrays for volatile organic compounds. Anal Chem. Jun. 1, 2006;78(11):3591-600.

Johnson et al., Active-site gating regulates substrate selectivity in a chymotrypsin-like serine protease the structure of haemophilus influenzae immunoglobulin A1 protease. J Mol Biol. Jun. 12, 2009;389(3):559-74. doi: 10.1016/j.jmb.2009.04.041. Epub Apr. 23, 2009.

Kalinska et al., Substrate specificity of *Staphylococcus aureus* cysteine proteases—Staphopains A, B and C. Biochimie. Feb. 2012;94(2):318-27. doi: 10.1016/j.biochi.2011.07.020. Epub Jul. 23, 2011.

Kaman et al., Evaluation of a FRET-Peptide Substrate to Predict Virulence in Pseudomonas aeruginosa. PLoS One; Nov. 2013;8(11):e81428, 10 pages.

Kasperkiewicz et al., Design of ultrasensitive probes for human neutrophil elastase through hybrid combinatorial substrate library profiling. PNAS. 2014;111:2518-23.

Kim et al., Applications of stable, nonradioactive isotope tracers in in vivo human metabolic research. Exp Mol Med. Jan. 2016; 48(1): e203. Epub Jan. 15, 2016. doi: 10.1038/emm.2015.97.

Kirkpatrick et al., Noninvasive lung cancer detection via pulmonary protease profiling. bioRxiv. 36 pages. doi: //doi.org/10.1101/495259.

Krebs et al., Molecular analysis of circulating tumour cells—biology and biomarkers. Nat Rev Clin Oncol. 2014;11:129-44.

Krilaviciute et al., Detection of cancer through exhaled breath?: a systematic review Literature search. Oncotarget. 2015;6:38643-57.

Kulkarni et al., MMP-9 Responsive PEG Cleavable Nanovesicles for Efficient Delivery of Chemotherapeutics to Pancreatic Cancer. Mol Pharm. Jul. 7, 2014; 11(7): 2390-2399. doi: 10.1021/mp500108p.

Kwak et al., Volatile disease biomarkers in breath: a critique. Curr Pharm Biotechnol; 2011;12:1067-74.

Kwon et al., Porous Silicon Nanoparticle Delivery of Tandem Peptide Anti?Infectives for the Treatment of Pseudomonas aeruginosa Lung Infections. Adv Mat. Sep. 20, 2017;29(35). 21pages.

Laupland et al., The changing culture of the microbiology laboratory. Can J Infect Dis Med Microbiol. 2013 Autumn; 24(3):125-128. doi: 10.1155/2013/101630.

Liou et al., Nonisotropic Enzyme-Inhibitor Interactions: A Novel Nonoxidative Mechanism for Quantum Proteolysis by Human Neutrophils. Biochem. 1995;34(49):16171-7.

Loynachan et al., ANYL 234: Catalytic nanomaterials for amplified biosensing. Abstract of Papers, 256th National Meeting & Exposition of the ACS. ACS National Meeting & Exposition. Aug. 19, 2018. 1 page.

Matsumoto et al., Role of bacterial proteases in pseudomonal and serratial keratitis. Biol Chem. Jan. 2004;385(11):1007-16.

McCarter et al., Substrate Specificity of the *Escherichia coli* Outer Membrane Protease OmpT. J Bacteriol. Sep. 2004; 186(17): 5919-5925. doi: 10.1128/JB.186.17.5919-5925.2004.

Meyer et al., Respiratory protease / antiprotease balance determines susceptibility to viral infection and can be modified by nutritional antioxidants. Am J Physiol Lung Cell Mol Physiol. 2015;308:L1189-L1201.

Morihara, Pseudolysin and other pathogen endopeptidases of thermolysin family. Methods in Enzymol. 1995;248:242-53.

Murray, What Is New in Clinical Microbiology—Microbial Identification by MALDI-TOF Mass Spectrometry. JMDI. 2012;14:419-23.

Nizio et al., In vitro volatile organic compound profiling using GCxGC-TOFMS to differentiate bacteria associated with lung infections: a proof-of-concept study. J Breath Res. Apr. 27, 2016;10:026008, 12 pages.

Ong et al., Inhalable nanosensors for rapid breath-based pathogen identification in respiratory infection. Adv Res Technol Symp. Mar. 5, 2018. 2 pages.

Ong et al., Use of Mass Spectrometric Vapor Analysis to Improve Canine Explosive Detection Efficiency. Anal Chem. 2017;89:6482-90.

Parks et al., Matrix metalloproteinases as modulators of inflammation and innate immunity. Nat Rev Immunol. Aug. 2004;4(8):617-29.

Patton et al., Inhaling medicines: delivering drugs to the body through the lungs. Nat Rev Drug Discov. Jan. 2007;6(1):67-74.

Patton et al., The lungs as a portal of entry for systemic drug delivery. Proc Am Thorac Soc. 2004;1(4):338-44.

(56) References Cited

OTHER PUBLICATIONS

Phillips et al., Variation in volatile organic compounds in the breath of normal humans. J Chromatogr B. 1999;729:75-88.

Potempa et al., Corruption of innate immunity by bacterial proteases. J Innate Immun. 2009;1(2):70-87.

Ross et al., Volatile compounds in blood headspace and nasal breath. J Breath Res. Sep. 13, 2017;11(4):046001, 12 pages. doi: 10.1088/1752-7163/aa7d10.

Roy et al., Matrix metalloproteinases as novel biomarkers and potential therapeutic targets in human cancer. J Clin Oncol. 2009;27:5287-97.

Sethi et al., Clinical application of volatile organic compound analysis for detecting infectious diseases. Clin Microbiol Rev. Jul. 2013;26(3):462-75. doi: 10.1128/CMR.00020-13.

Shaw et al., The role and regulation of the extracellular proteases of *Staphylococcus aureus*. Microbiol. Jan. 2004;150:217-28. doi: 10.1099/mic.0.26634-0.

Shibuya et al., Pseudomonas aeruginosa alkaline proteinase might share a biological function with plasmin. Biochim Biophys Acta. Apr. 29, 1991; 1077(3):316-24.

Stach et al., Unique Substrate Specificity of SplE Serine Protease from *Staphylococcus aureus*. Structure. Apr. 3, 2018;26(4):572-579.e4. doi: 10.1016/j.str.2018.02.008. Epub Mar. 8, 2018.

Sweeney et al., Robust classification of bacterial and viral infections via integrated host gene expression diagnostics. Sci Transl Med. Jul. 2016;8(346):346ra91.

Thomassin et al., OmpT Outer Membrane Proteases of Enterohemorrhagic and Enteropathogenic *Escherichia coli* Contribute Differently to the Degradation of Human LL-37. Infect Immun. Feb. 2012; 80(2): 483-492. doi: 10.1128/IAI.05674-11.

Van Der Schee et al., Breathomics in lung disease. Chest. 2015;147:224-31.

Vessillier et al., Hydrolysis of glycine-containing elastin pentapeptides by LasA, a metalloelastase from Pseudomonas aeruginosa. Eur J Biochem. Feb. 2001;268(4):1049-57.

Wang et al., Intrinsic enzyme mimicking activity of gold nanoclusters upon visible light triggering and its application for colorimetric trypsin detection. Biosens Bioelectronics. 2015;64:523-9. Epub Sep. 30, 2014.

Warren et al., Disease detection by ultrasensitive quantification of microdosed synthetic urinary biomarkers. J Am Chem Soc. 2014;136:13709-14.

Warren et al., Harnessing protease activity to improve cancer care. Annual Rev Cancer Biol. 2018;2:353-76.

Wildeboer et al., Characterization of bacterial proteases with a panel of fluorescent peptide substrates. Anal Biochem. Jan. 15, 2009;384(2):321-8. doi: 10.1016/j.ab.2008.10.004. Epub Oct. 11, 2008.

Wilkinson et al., Ventilator-Associated Pneumonia Is Characterized by Excessive Release of Neutrophil Proteases in the Lung. Chest. Dec. 2012;142(6):1425-32.

Wilson et al., Applications and Advances in Electronic-Nose Technologies. Sensors (Basel). 2009;9(7):5099-148. doi: 10.3390/s90705099. Epub Jun. 29, 2009.

Zheng et al., Dual-reaction triggered sensitivity amplification for ultrasensitive peptide-cleavage based electrochemical detection of matrix metalloproteinase-7. Biosens Bioelectronics. 2018;103:46-52. Epub Feb. 21, 2018.

Zhou et al., Thermo-sensitive microgels supported gold nanoparticles as temperature-mediated catalyst. Chinese J Polym Sci. 2019;37:235-42. Epub Aug. 30, 2018.

Zhu et al., Detecting bacterial lung infections: in vivo evaluation of in vitro volatile fingerprints. J Breath Res. Jan. 10, 2013;7(1):016003, 7 pages.

Zumla et al., Rapid point of care diagnostic tests for viral and bacterial respiratory tract infections—needs, advances, and future prospects. Lancet Infect Dis. 2014;14(11):1123-35.

DQ™Gelatin From Pig Skin, Fluorescein Conjugate—Special Packaging. ThermoFisher Scientific ENZCHEK® Gelatinase/Collagenase Assay Kit Product Information Sheet. Accessed on Jul. 14, 2020. Retrieved from: ://www.thermofisher.com/order/catalog/product/D12054#/D12054>. 4 pages.

Harris et al., Protease-triggered unveiling of bioactive nanoparticles. Small. 2008;4(9):130712. doi: 10.1002/smll.200701319. Epub Aug. 8, 2008.

Jiang et al., Tumor imaging by means of proteolytic activation of cell-penetrating peptides. Proc. Natl. Acad. Sci. U. S. A. 2004;101:17867-17872.

Olson et al., In vivo characterization of activatable cell penetrating peptides for targeting protease activity in cancer. Integr Biol (Camb). 2009;1:382-93.

Vandooren et al., Zymography Methods for Visualizing Hydrolytic Enzymes. Nat Methods. Mar. 2013;10(3):211-20. doi: 10.1038/nmeth.2371.

Vasiljeva et al., Monitoring protease activity in biological tissues using antibody prodrugs as sensing probes. Sci Rep. Apr. 3, 2020;10(1):5894.

Yan et al., In Situ Zymography: A Molecular Pathology Technique to Localize Endogenous Protease Activity in Tissue Sections. Vet Pathol May 2003 ;40(3):227-36.

\* cited by examiner

LC/MS/MS DETECTION OF PROTEOLYTIC REPORTERS

| Fluor-(PEPTIDE SEQUENCE)-NP | EXPECTED CLEAVAGE PRODUCT* | OBSERVED MAJOR CLEAVAGE PRODUCT* | EXPECTED MASS | OBSERVED MASS | PROTEASE ACTIVATION (MS)** | PROTEASE ACTIVATION (FLUORESCENCE)** |
|---|---|---|---|---|---|---|
| Fluor-dS-dK-G-G-P-Q-G-I-W-G-Q-C-(NP) | GGPQG | GGPQG | 987.4 | 987.4 | 2,7,8,9 | 2,7,8,9 |
| Fluor-dS-dK-G-G-P-L-G-V-R-G-K-C-(NP) | GGPLG | GGPLG | 972.4 | 972.4 | 2,7,8,9,th | 2,7,9 |
| Fluor-dS-dK-G-G-P-L-A-Nva-Dpa-A-R-G-C-(NP) | GGPLA | GGPLA | 986.4 | 986.4 | 2,7,8,9 | 2,7,8,9,14,th |
| Fluor-dS-dK-G-G-P-V-G-L-I-G-C-(NP) | GGPVG | GGPVG | 958.4 | 958.4 | 2,7,8,9,14 | 7,9 |
| Fluor-dS-dK-G-G-P-V-P-L-S-L-V-M-C-(NP) | GGPVPLS | GGPVP | 1198.7 | 998.4 | 7,8,9,th | 7,8 |
| Fluor-dS-dK-G-G-S-G-P-L-G-L-R-S-W-C-(NP) | GGSGGPLG | GGSGGPLG | 1173.5 | 1173.5 | 7,9,14,th | 7,8,9,th |
| Fluor-dS-dK-G-G-P-W-G-I-W-G-Q-G-C-(NP) | GGGPWG | GGGPWG | 1024.4 | 1024.4 | 2,7,8,9 | 2,7,8,9 |
| Fluor-dS-dK-G-G-dF-Pip-R-S-G-G-G-C-(NP) | GGdFRipR | GGdFRipR | 1119.5 | 1119.5 | th | th |
| Fluor-dS-dK-G-G-L-V-P-R-G-S-G-C-(NP) | GGLVP | GGLVP | 1170.5 | 1170.5 | th | th |

*ALL PEPTIDES HAVE Fluor-dS-dK-[VARIABLE GROUP]; ONLY THE [VARIABLE GROUP] ARE SHOWN IN THESE COLUMNS
**2 = MMP-2,7; 7,8 = MMP-7,8; 8,9 = MMP-8,9; 9,14 = MMP-9,14; th = THROMBIN

Fig. 4

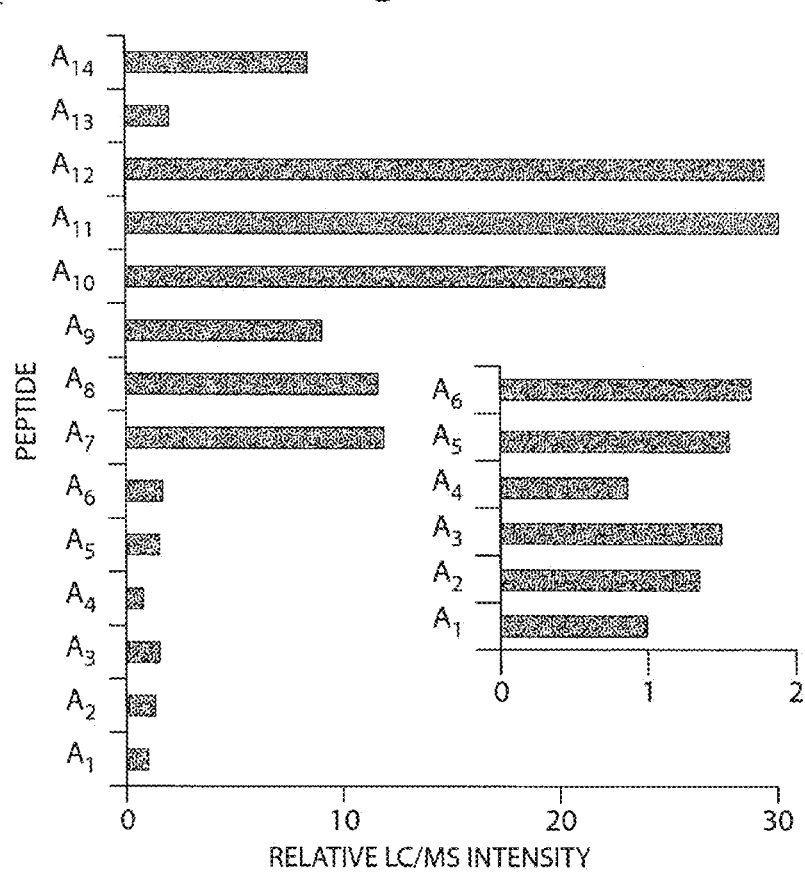

| PEPTIDE | SEQUENCE |
|---|---|
| $A_1$ | Fl-dR-G-G-dS-G-G-dS-G-G-dS-dR-V-V-V-L-S |
| $A_2$ | Fl-dR-G-G-dS-G-G-dS-dR-G-G-V-V-V-L-S |
| $A_3$ | Fl-dR-G-G-dS-dR-G-G-dS-G-G-V-V-V-L-S |
| $A_4$ | Fl-dR-G-G-dS-dR-G-G-V-V-V-L-S |
| $A_5$ | Fl-dR-G-dS-dR-G-G-V-V-V-L-S |
| $A_6$ | Fl-dR-dS-dR-G-G-V-V-V-L-S |
| $A_7$ | Fl-dR-G-G-dS-G-G-dS-G-G-dS-dR-P-V-G |
| $A_8$ | Fl-dR-G-G-dS-G-G-dS-dR-G-G-P-V-G |
| $A_9$ | Fl-dR-G-G-dS-dR-G-G-dS-G-G-P-V-G |
| $A_{10}$ | Fl-dR-G-G-dS-dR-G-G-P-V-G |
| $A_{11}$ | Fl-dR-G-dS-dR-G-G-P-V-G |
| $A_{12}$ | Fl-dR-dS-dR-G-G-P-V-G |
| $A_{13}$ | Fl-dR-G-G-dS-G-G-dS-G-G-dF-Pip-R |
| $A_{14}$ | Fl-dR-G-G-dS-G-G-dF-Pip-R |

METHODS AND PRODUCTS FOR IN VIVO ENZYME PROFILING

RELATED APPLICATIONS

This application is a divisional of U.S. application Ser. No. 14/166,481, filed Jan. 28, 2014, entitled "METHODS AND PRODUCTS FOR IN VIVO ENZYME PROFILING", which is a continuation of U.S. application Ser. No. 12/715,965, filed on Mar. 2, 2010, now issued as U.S. Pat. No. 8,673,267 on Mar. 18, 2014, which claims the benefit under 35 U.S.C. § 119(e) of U.S. Provisional Application No. 61/156,660, filed on Mar. 2, 2009, both entitled "Methods and Products for In Vivo Enzyme Profiling," the entire contents of each of which are incorporated herein by reference.

GOVERNMENT SUPPORT

This invention was made with Government support under Grant No. R01 CA124427 awarded by the National Institutes of Health (NIH). The Government has certain rights in the invention.

FIELD OF THE INVENTION

The present invention relates to methods and products associated with in vivo enzyme profiling. Some aspects of the present invention relate to profiling enzymatic reaction products. In particular, the invention relates to methods of in vivo processing of exogenous molecules followed by detection of signature molecules as representative of the presence or absence of active enzymes associated with disease or conditions. The invention also relates to products, kits, and databases for use in the methods of the invention.

BACKGROUND OF THE INVENTION

Dysregulation of proteases in cancer has important consequences in cell signaling and helps drive cancer cell proliferation, invasion, angiogenesis, avoidance of apoptosis, and metastasis. Currently, in vivo analysis of proteases (and other enzymes such as glycosidase, esterase, etc.) activity is limited to biopsy or local fluorescent techniques, which are hindered by their invasiveness or low multiplexing potential, respectively.

SUMMARY OF THE INVENTION

The invention in some aspects is a method involving administering to a subject a pro-diagnostic reagent, wherein the pro-diagnostic reagent comprises a modular structure having a carrier domain linked to a signature producing domain, wherein the signature producing domain is capable of producing a signature molecule in the subject; identifying a biological sample for detection of the signature molecule, wherein the biological sample is at a site remote from the production of the signature molecule; and, subjecting the biological sample to an analysis method in order to detect the presence of the signature molecule, wherein the presence of the signature molecule in the biological sample is indicative of a biological predictor molecule within the subject.

In one embodiment the signature producing domain comprises an enzyme susceptible domain linked to a signature molecule, wherein the biological predictor molecule is an enzyme, wherein the enzyme susceptible domain is susceptible to modification by the enzyme in the subject, and wherein the presence of the signature molecule in the biological sample is indicative of an active enzyme within the subject.

In another embodiment the signature producing domain comprises an active signature producing agent, wherein the active signature producing agent is capable of modifying the biological predictor molecule to produce the signature molecule in the subject. The active signature producing agent may be an enzyme, such as a protease or a glycosidase.

In other embodiments the pro-diagnostic reagent further comprises an implantable microdelivery device that houses the modular structure. The implantable microdelivery device in some embodiments is an implantable capsule with a semi-permeable membrane that encapsulates the modular structure. In other embodiments the implantable microdelivery device is a chip having the modular structure attached thereto. In yet other embodiments the implantable microdelivery device is a sustained-release formulation.

In some aspects the invention is a method involving administering to a subject a pro-diagnostic reagent, wherein the pro-diagnostic reagent comprises a carrier domain linked to an enzyme susceptible domain which is linked to a signature molecule, wherein the enzyme susceptible domain is susceptible to modification by an enzyme in the subject; identifying a biological sample for detection of the signature molecule, wherein the biological sample is at a site remote from the enzyme; and, subjecting the biological sample to an analysis method in order to detect the presence of one or more signature molecules, wherein the presence of the signature molecule in the biological sample is indicative of an active enzyme within the subject.

In other aspects of the invention a method of administering to a subject a pro-diagnostic reagent, wherein the pro-diagnostic reagent comprises a carrier domain linked to an enzyme susceptible domain which is linked to a signature molecule; collecting a urine sample from the subject; and, subjecting the urine sample to an analysis method in order to detect the presence of the signature molecule, wherein the presence of the signature molecule in the biological sample is indicative of an active enzyme within the subject is provided.

In yet other aspects a method for diagnosing a disease is provided. The method involves administering to a subject a pro-diagnostic reagent, wherein the pro-diagnostic reagent comprises a carrier domain linked to an enzyme susceptible domain which is linked to a signature molecule, and wherein the enzyme susceptible domain is susceptible to cleavage by an enzyme associated with a disease; collecting a urine sample from the subject; and, subjecting the urine sample to an analysis method in order to detect the presence of the signature molecule, wherein the presence of the signature molecule in the biological sample is indicative of the subject having the disease.

In another aspect of the invention a method of collecting a urine sample from a subject suspected of having a disorder or condition, wherein the subject has been administered a pro-diagnostic reagent, the pro-diagnostic reagent comprising a carrier domain linked to an enzyme susceptible domain which is linked to a signature molecule; and, subjecting the urine sample to a multiplex analysis method in order to detect the presence of the signature molecule, wherein the presence of the signature molecule in the biological sample is indicative of the disorder or condition within the subject. is provided In some embodiments, the subject is a healthy subject. In some embodiments, the subject is a subject at risk of developing a disease or condition. In some embodiments, the subject is suspected of having a disease or condition or a subject diagnosed with having a disease or condition.

A method of collecting a urine sample from a subject suspected of having a disorder or condition, wherein the subject has been administered a pro-diagnostic reagent, the pro-diagnostic reagent comprising a carrier domain linked to an enzyme susceptible domain which is linked to a signature molecule and, subjecting the urine sample to a multiplex analysis method in order to detect the presence or absence of the signature molecule, wherein the absence of the signature molecule in the biological sample is indicative of the disorder or condition within the subject is provided according to other aspects of the invention.

A method of treating a subject is provided according to an aspect of the invention. The method involves collecting a urine sample from a subject suspected of having a disorder or condition or diagnosed with a disorder or condition, wherein the subject has been administered a pro-diagnostic reagent, the pro-diagnostic reagent comprising a carrier domain linked to an enzyme susceptible domain which is linked to a signature molecule; subjecting the urine sample to a multiplex analysis method in order to detect the presence of the signature molecule, wherein the presence of the signature molecule in the biological sample is indicative of the disorder or condition within the subject; and, administering a therapeutic agent to the subject to treat the disorder.

In some embodiments a further step of collecting a biological sample from the subject is provided. In other embodiments the signature molecule is detected in the biological sample in the subject. The biological sample may be urine, blood, saliva, or mucous secretion.

A plurality of pro-diagnostic reagents having a plurality of signature molecules may be administered to the subject in some embodiments. The plurality of pro-diagnostic reagents may have a plurality of signature molecules. In other embodiments the pro-diagnostic reagent includes a plurality of signature molecules.

In some embodiments the enzyme susceptible domain is susceptible to modification, i.e. cleavage, addition, conformational or charge change, by an enzyme associated with a disease or condition. In some embodiments the enzyme susceptible domain is susceptible to cleavage by a protease associated with a disease or condition. The enzyme susceptible domain in other embodiments is susceptible to modification by an enzyme not associated with a disease or condition, but associated with a normal condition.

In some embodiments the enzyme susceptible domain is a peptide, such as, for instance, a MMP sensitive site, a kallikrein sensitive site, a cathepsin sensitive site, a plasminogen activator sensitive site and/or an ADAM sensitive site.

In some embodiments the disease or condition is cancer, cardiovascular disease, arthritis, viral, bacterial, parasitic or fungal infection, Alzheimer's disease emphysema, thrombosis, hemophilia, stroke, organ dysfunction, any inflammatory condition, vascular disease, parenchymal disease, or a pharmacologically-induced state.

In some embodiments, the carrier domain comprises a particle, for example, a microparticle or a nanoparticle. The carrier domain is greater than 5 nm in size in some embodiments and in other embodiments is smaller than 5 nm in size. In some embodiments, the carrier domain comprises a targeting domain and/or a therapeutic agent. In some embodiments, the carrier domain selectively interacts with a molecular target, for example, a protein or peptide, a nucleic acid, or a carbohydrate. In some embodiments, the carrier domain selectively binds a molecular target. In some embodiments, the carrier domain selectively interacts with a target molecule as part of an enzymatic reaction, for example, an enzymatic reaction carried out by the carrier domain or by the target molecule. In some embodiments, the carrier domain comprises a peptide, a protein, a nucleic acid or a small molecule, for example, a peptide, protein, nucleic acid or small molecule selectively binding a molecular target, for example, a target molecule (e.g., a peptide, protein, nucleic acid, or carbohydrate) expressed in a target cell or cell type, after administration to a subject. In some embodiments the molecular target is specifically expressed in a target cell or target cell type, for example, a cancer cell or a cell of a certain differentiation state or of a certain tissue. In some embodiments, the carrier domain comprises a therapeutic agent. In some embodiments, the carrier domain comprises a therapeutic agent selectively interacting with a molecular target, for example, a molecular target expressed in a target cell or target cell type. In some embodiments the carrier domain is a nanoparticle, a peptide, for example, an RGD peptide, an aptamer, an antibody, or a fragment thereof, an adnectin, or a targeting molecule.

The signature molecule in some embodiments is a peptide, nucleic acid, small molecule, fluorophore/quencher, carbohydrate, particle, radiolabel, MRI-active compound, inorganic material, and/or organic material, with encoded characteristics to facilitate optimal detection.

The analysis step used in the methods may be a multiplex analysis method or a singular analysis method. The analysis methods include but are not limited to mass spectrometry, liquid chromatography-mass spectrometry, PCR analysis, DNA microarray, and fluorescence analysis.

In some embodiments the method also includes a purification step, wherein the signature molecule is isolated from other components in the biological sample. The purification step may be, for instance, affinity chromatography.

In other aspects of the invention a reagent is provided. The reagent includes a carrier domain, wherein the carrier domain is a particle and is greater than 5 nm in size; an enzyme susceptible domain linked to the carrier domain; and, a signature molecule linked to the enzyme susceptible domain, wherein the signature molecule is a peptide or nucleic acid.

In other aspects, the invention is a reagent having an implantable microdelivery device housing a modular structure having a carrier domain linked to a signature producing domain.

In some embodiments the signature producing domain comprises an active signature producing agent, wherein the active signature producing agent is capable of modifying a biological predictor molecule to produce a signature molecule. The active signature producing agent may be an enzyme such as a protease or a glycosidase. In other embodiments the implantable microdelivery device is an implantable capsule with a semi-permeable membrane that encapsulates the modular structure, a chip having the modular structure attached thereto, or a sustained-release formulation.

In other aspects the invention is a reagent including a carrier domain having a plurality of enzyme susceptible domains linked to the carrier domain wherein each enzyme susceptible domain is linked to a non-fluorescent signature molecule.

In yet other aspects the invention is a composition having a plurality of pro-diagnostic reagents comprising a carrier domain, an enzyme susceptible domain linked to the carrier domain; and, a non-fluorescent signature molecule linked to the enzyme susceptible domain.

In some embodiments the carrier domain is polymer based microparticle, an iron oxide microparticle, or nanoparticle, an inorganic carrier, or an organic carrier. The carrier domain optionally includes a targeting domain and/or a therapeutic agent. The targeting domain may be, for instance, an antibody.

In some embodiments the enzyme susceptible domain is a peptide, such as for instance, GGPQGIWGQC (SEQ ID NO: 1), GGPLGVRGKC (SEQ ID NO: 2), GGPLANvaDpaARGC (SEQ ID NO: 3), GGPVGLIGL (SEQ ID NO: 4), GGPVPLSLVMC (SEQ ID NO: 5), GGSGGPLGLRSWC (SEQ ID NO: 6), GGGPWGIWGQGC (SEQ ID NO: 7), GGdFPipRSGGGC (SEQ ID NO: 8), or GGLVPRGSGC (SEQ ID NO: 9).

In other embodiments the signature molecule is a peptide, nucleic acid, small molecule, fluorophore/quencher, carbohydrate, or particle. The signature molecule in some embodiments is a peptide of GGPQG (SEQ ID NO: 10), GGPLG (SEQ ID NO: 11), GGPLA (SEQ ID NO: 12), GGPVG (SEQ ID NO: 13), GGPVPLS (SEQ ID NO: 14), GGSGGPLG (SEQ ID NO: 15), GGGPWG (SEQ ID NO: 16), GGdFPipR (SEQ ID NO: 17), or GGLVP (SEQ ID NO: 18).

A kit is provided according to other aspects of the invention. The kit has a container housing a pro-diagnostic reagent, wherein the pro-diagnostic reagent comprises a carrier domain linked to an enzyme susceptible domain which is linked to a signature molecule; and, instructions for administering the pro-diagnostic reagent to a subject and for analyzing the signature molecule of the pro-diagnostic reagent in a biological sample of the subject.

In some embodiments the kit also includes a second container housing an analytical reagent. In other embodiments the kit also includes a box housing the containers. In yet other embodiments the kit includes a specimen collection device. Other embodiments of this invention would use a diversity of carriers, cleavage domains, and signature molecules to enable detection via modalities such as radiation, fluorescence, color, elemental detection, light scattering, magnetic techniques, MRI, electrical measurements, biochemical measurements, biological assays (including ELISA assays and others), among others.

Each of the embodiments of the invention can encompass various recitations made herein. It is, therefore, anticipated that each of the recitations of the invention involving any one element or combinations of elements can, optionally, be included in each aspect of the invention.

BRIEF DESCRIPTION OF THE DRAWINGS

FIG. 2A is a schematic of the pro-diagnostic reagent, with the circles referring to the carrier, the star is a fluorescent molecule, and the zigzag line refers to the enzyme susceptible domain and the signature molecule (darker end region). FIG. 2B is an electron micrograph of the pro-diagnostic reagent. FIG. 2C is a graph depicting the circulation time of the pro-diagnostic reagent, by plotting detection of the carrier in the blood with respect to time after intravenous injection. FIG. 2D is photographs of mice having either tumors or injuries (left and right panels, respectively) administered the pro-diagnostic reagent. FIG. 2E is histopathological analysis of carrier homing to tumors or regions of injury.

FIG. 4 is a Table depicting the mass detection of ejected fragments in vitro. The results confirmed that the fluorescent results from the screen could also be detected by analyzing the mass of ejected fragments in vitro.

FIG. 5A is a schematic of the pro-diagnostic reagent as shown in FIG. 3A, further depicting the portion of the molecule that undergoes renal clearance and the portion that undergoes RES clearance. FIG. 5B is a set of photographs of that were intravenously administered the optimized pro-diagnostic reagent for injury detection (top) or tumor detection (bottom). Half the mice that were administered the optimized pro-diagnostic agents for injury-detection suffered bilateral hind limb injuries (left side of the photograph) while the control mice had no injuries (right side of the photograph). Half the mice administered the optimized pro-diagnostic agents for tumor-detection harbored human fibrosarcoma tumors (HT-1080) (left side of photograph), while the other mice contained no tumors (right side of photograph). FIG. 5C is a set of graphs depicting relative bladder fluorescence for tumor (bottom panel) or injured (top panel) versus control mice in order to track the entrance of cleaved signature peptide into the urine after injection.

FIG. 6A is a photograph of an experimental mouse, having bilateral injury and a control uninjured mouse. FIG. 6B is a graph depicting the ratio of signature molecule (from thrombin cleavable proteolytic susceptible domain) to isotopically labeled product in injured versus control mice.

FIG. 8A shows representative proteolytic products appended with peptide caps of differing length and charge density. FIG. 8B is a graph showing normalized relative intensities of the peptide reporters. The inset of FIG. 8B shows a magnification of the normalized relative intensities of the peptide sequences A1-A6 as measured via LC/MS.

BRIEF DESCRIPTION OF THE SEQUENCES

SEQ ID NO: 1 is GGPQGIWGQC

SEQ ID NO: 2 is GGPLGVRGKC

SEQ ID NO: 3 is GGPLANvaDapARGC

SEQ ID NO: 4 is GGPVGLIGL

SEQ ID NO: 5 is GGPVPLSLVMC

SEQ ID NO: 6 is GGSGGPLGLRSWC

SEQ ID NO: 7 is GGGPWGIWGQGC

SEQ ID NO: 8 is GGdFPipRSGGGC

SEQ ID NO: 9 is GGLVPRGSGC

SEQ ID NO: 10 is GGPQG

SEQ ID NO: 11 is GGPLG

SEQ ID NO: 12 is GGPLA

SEQ ID NO: 13 is GGPVG

SEQ ID NO: 14 is GGPVPLS

SEQ ID NO: 15 is GGSGGPLG

SEQ ID NO: 16 is GGGPWG

SEQ ID NO: 17 is GGdFPipR

SEQ ID NO: 18 is GGLVP

SEQ ID NO: 19 is GGVVVLS

SEQ ID NO: 20 is Fl-dR-dS-dR

SEQ ID NO: 21 is Fl-dR-G-dS-dR

SEQ ID NO: 22 is Fl-dR-dS-dR-G-G-P-Q-G-I-W-G-Q-C

SEQ ID NO: 23 is Fl-dR-G-dS-dR-G-G-P-L-G-V-R-G-K-C

SEQ ID NO: 24 is Fl-dR-G-dS-dR-G-G-P-L-A-Nva-Dpa-A-R-G-C

SEQ ID NO: 25 is Fl-dR-G-dS-dR-G-G-P-V-G-L-I-G-C

SEQ ID NO: 26 is Fl-dR-dS-dR-G-G-P-V-P-L-S-L-V-M-C

SEQ ID NO: 27 is Fl-dR-G-dS-dR-G-G-V-V-V-L-S-M-T-A-C

SEQ ID NO: 28 is Fl-dR-G-dS-dR-G-G-S-G-G-P-L-G-L-R-S-W-C

SEQ ID NO: 29 is Fl-dR-G-dS-dR-G-G-G-P-W-G-I-W-G-Q-G-C

SEQ ID NO: 30 is Fl-dR-G-G-dS-G-G-dF-Pip-R-S-G-G-G-C

SEQ ID NO: 31 is Fl-dR-dS-dR-G-G-L-V-P-R-G-S-G-C

BRIEF DESCRIPTION OF THE SEQUENCES

SEQ ID NO: 32 is Fl-dR-G-G-dS-G-G-F-P-R-S-G-G-G-C

SEQ ID NO: 33 is Fl-dR-G-G-dS-G-G-G-dF-Pip-K-S-G-G-G-C

SEQ ID NO: 34 is Fl-dR-G-G-dS-G-G-G-dF-P-K-S-G-G-C

SEQ ID NO: 35 is dR-dS-dR

Figure 1A:
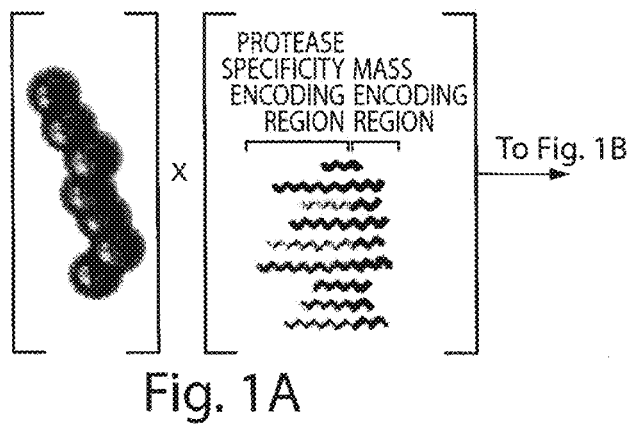
FIGS. 1A-1C are s a schematic depicting a method according to the invention for multiplexed in vivo enzyme profiling of mass-coded nanoparticle based pro-diagnostic reagents.

SEQ ID NO: 36 is dR-G-dS-dR (Fl: Fluorescein; Nva: Norvaline; Dap = (N-β-(2,4-dinitrophenyl))-L-α,β-diaminopropionic acid); Pip: pipecolic acid; d: D-isomer.)

SEQ ID NO: 31 is Fl-dR-dS-dR-G-G-L-V-P-R-G-S-G-C
SEQ ID NO: 32 is Fl-dR-G-G-dS-G-G-F-P-R-S-G-G-G-C
SEQ ID NO: 33 is Fl-dR-G-G-dS-G-G-G-dF-Pip-K-S-G-G-C
SEQ ID NO: 34 is Fl-dR-G-G-dS-G-G-G-dF-P-K-S-G-G-C
SEQ ID NO: 35 is dR-dS-dR
SEQ ID NO: 36 is dR-G-dS-dR (Fl: Fluorescein; Nva: Norvaline; Dap=(N-β-(2,4-dinitrophenyl))-L-α,β-diaminopropionic acid); Pip: pipecolic acid; d: D-isomer.)

DETAILED DESCRIPTION OF THE INVENTION

The status of physiological conditions of a subject can be assessed using the methods of the invention by identifying molecular properties also referred to as "molecular signatures". Such molecular signatures are useful for diagnosing diseases such as cancer, rheumatoid arthritis and arteriosclerosis, as well as for prognostic indicators. The response of most cancers to medical intervention is currently monitored by physical exams and various clinical imaging modalities. A few cancers such as prostate and ovarian cancer are monitored by use of single biomarkers in the blood. Such diagnostic techniques are achieved, for instance using fluorescence detection of molecular markers which are activated in a particular disease state.

The invention relates to a platform for functional characterization of disease or condition specific enzymatic repertoire as a method to monitor both disease progression and regression as well as response to therapeutics. The methods provide orders of magnitude more in vivo enzyme-substrate information than current fluorescent detection technologies. The platform provides a unique opportunity to functionally monitor cancer and other disease progression and response to therapy. It is particularly useful for prolonged therapeutic regimens, where the discovery of prognostic functional signatures would greatly assist intervention and where enzymatic signatures directly correlate to therapeutic efficacy.

By administering a pro-diagnostic reagent, such as an exogenous detectable substrate library into animal models of disease it is possible to gain information into substrate specific enzymatic activities associated with diseases, such as cancer, cardiovascular disease, arthritis, and others. The technology allows for the potential simultaneous profiling of hundreds of enzyme-substrate activities in vivo using, for instance, -chaperoned, enzyme sensitive detectable compounds, an example of a compound referred to as pro-diagnostic reagents. The method leverages the distinct pharmacokinetics of modular structures and small, optionally hydrophilic, marker peptides (RES and renal clearance, respectively). The pro-diagnostic reagents have long circulation times and thus remain in circulation or permeate into tumors via porous angiogenic vascular networks, where upon local molecules, such as enzymes (MMPs, kallikreins, cathepsins, plasminogen activators, ADAMs) gain access to the enzyme susceptible regions of the pro-diagnostic reagents or substrates gain access to the enzymes of the pro-diagnostic reagents.

When the pro-diagnostic reagents, for example, the reagents including an enzyme susceptible domain are exposed to enzymes, for instance, proteases, the reagent is cleaved, such that a marker, referred to herein as a signature molecule, is released. The marker is renally-cleared and thus functions as a "messenger" of enzyme activity. For instance, a marker may include a self-quenched dye, such as Cy5.5 which is bound to a larger molecule. When the peptide containing the self-quenched dye is cleaved or modified by specific enzymes at the disease site the fluorophores are no longer self-quenched but instead developed fluorescent properties which can be detected at remote sites. Alternatively, using mass-encoded substrate libraries, the mass of enzyme substrates are designed such that upon cleavage, a distinct mass-specific messenger of cleavage will enter the urine of a patient or animal for detection using LC-MS technology. LC-MS urine analysis can generate data that is organized into a barcode of, for instance, cancer enzyme activity. In the absence of enzyme activity the pro-diagnostic reagents remain uncleaved and the whole reagent including the signature molecule is cleared through RES organs (liver, spleen, and lymph nodes) without producing urine markers. The use of mass to identify substrates allows unprecedented multiplexing capability with the potential to assay greater than 1,000 substrates.

When the pro-diagnostic reagents includes an enzyme, such as a protease, the enzyme is exposed to endogenous substrates and the substrate is cleaved, such that a marker, referred to herein as a signature molecule, is released from the endogenous substrate. The marker is renally-cleared and thus functions as a "messenger" of enzyme activity. For instance, a marker may include a peptide, carbohydrate or nucleic acid fragment which has been cleaved from the substrate. Using the detection techniques, for instance, LC-MS technology, the mass of the signature can be detected. LC-MS urine analysis can generate data that is organized into a barcode of, for instance, cancer enzyme/substrate activity. In the absence of enzyme activity the signature molecule is not cleared through RES organs (liver, spleen, and lymph nodes) and does not produce urine markers.

Thus, the invention in some aspects involves administering to a subject a pro-diagnostic reagent, identifying a biological sample from the subject in which to detect the signature molecule and optionally collecting the sample; and, subjecting the biological sample to an analysis method in order to detect the presence of one or more signature molecules. The presence of the signature molecule in the biological sample is indicative of an active enzyme or a substrate within the subject.

For example the invention in some aspects involves methods for administering to a subject a pro-diagnostic reagent, such that the pro-diagnostic reagent has a modular structure having a carrier domain linked to a signature producing domain, wherein the signature producing domain is capable of producing a signature molecule in the subject; identifying a biological sample for detection of the signature molecule, wherein the biological sample is at a site remote from the production of the signature molecule; and, subjecting the biological sample to an analysis method in order to detect the presence of the signature molecule, wherein the presence of the signature molecule in the biological sample is indicative of a biological predictor molecule within the subject.

The pro-diagnostic reagent comprises a modular structure having a carrier domain linked to a signature producing domain. A modular structure, as used herein, refers to a molecule having multiple domains.

The signature producing domain may be, for instance, an enzyme that can react with an endogenous substrate in a subject to produce a signature molecule or it may be an enzyme susceptible domain which is linked to a signature molecule. The carrier domain may include a single type of signature producing domain, such as, a single enzyme susceptible domain and or signature molecule or it may include multiple signature producing domains, such as, different enzyme susceptible domains and signature molecules. For instance each carrier may include 1 type of signature producing domain or it may include 2-1,000 different signature producing domains or any integer therebetween. Alternatively each carrier may include greater than 1,000 signature producing domains. Multiple copies of the pro-diagnostic reagent are administered to the subject. Some mixtures of pro-diagnostic reagents may include signature producing domains that are enzymes, others may be enzymatic susceptible domains, and other may be mixtures of the two. Additionally a plurality of different pro-diagnostic reagents may be administered to the subject to determine whether multiple enzymes and/or substrates are present. In that instance, the plurality of different pro-diagnostic reagents includes a plurality of signature molecules, such that each enzyme susceptible domain is associated with a particular signature molecule or molecules.

The carrier domain may serve as the core of the pro-diagnostic agent. A purpose of the carrier domain is to serve as a platform for the signature producing domain. As such, the carrier can be any material or size as long as it can serve as a carrier or platform. Preferably the material is non-immunogenic, i.e. does not provoke an immune response in the body of the subject to which it will be administered. Another purpose is that it may function as a targeting means to target the modular structure to a tissue, cell or molecule. In some embodiments the carrier domain is a particle. A particle, for example, a nanoparticle, may, for instance, result in passive targeting to tumors by circulation. Other types of carriers, include, for instance, compounds that cause active targeting to tissue, cells or molecules. Examples of carriers include, but are not limited to, microparticles, nanoparticles, aptamers, peptides (RGD, iRGD, LyP-1, CREKA, etc.) antibodies or antibody fragments (e.g. herceptin, cetuximab, panitumumab, etc.) and small molecules (e.g. erlotinib, gefitinib, sorafenib, etc.).

As used herein the term "particle" includes nanoparticles as well as microparticles. Nanoparticles are defined as particles of less than 1.0 µm in diameter. A preparation of nanoparticles includes particles having an average particle size of less than 1.0 µm in diameter. Microparticles are particles of greater than 1.0 µm in diameter but less than 1 mm. A preparation of microparticles includes particles having an average particle size of greater than 1.0 µm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments the diameter is about 5 nm to about 500 nm. In other embodiments, the diameter is about 100 nm to about 200 nm. In other embodiment, the diameter is about 10 nm to about 100 nm.

The particles may be composed of a variety of materials including ceramic, metallic, natural polymer materials (including lipids, sugars, chitosan, hyaluronic acid etc), synthetic polymer materials (including poly-lactide-coglycolide, poly-glycerol sebacate, etc), and non-polymer materials, or combinations thereof.

The particles may be composed in whole or in part of polymers or non-polymer materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxyapatite, tricalcium phosphate, dicalcium phosphate, tricalcium phosphate, tetracalcium phosphate, amorphous calcium phosphate, octacalcium phosphate, and silicates. In certain embodiments the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide.

A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, Acc. Chem. Res. 33:94, 2000; Langer, J. Control Release 62:7, 1999; and Uhrich et al., Chem. Rev. 99:3181, 1999; all of which are incorporated herein by reference).

Polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof.

PVP is a non-ionogenic, hydrophilic polymer having a mean molecular weight ranging from approximately 10,000 to 700,000 and the chemical formula $(C6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyethylene glycol (PEG), also known as poly(oxyethylene) glycol, is a condensation polymer of ethylene oxide and water having the general chemical formula $HO(CH_2CH_2O)[n]H$.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, PVA and PVP are commercially available from chemical suppliers such as the Sigma Chemical Company (St. Louis, Mo.).

In certain embodiments the particles may comprise poly (lactic-co-glycolic acid) (PLGA).

The carrier may be composed of inorganic materials. Inorganic materials include, for instance, magnetic materials, conductive materials, and semiconductor materials.

In addition to particles the carrier may be composed of any organic carrier, including biological and living carriers such as cells, viruses, bacteria, as well as any non-living organic carriers, or any composition enabling exposure of enzyme substrates to enzymes in disease (including extracellular, membrane-bound, and intracellular enzymes).

In some embodiments, the particles are porous. A porous particle can be a particle having one or more channels that extend from its outer surface into the core of the particle. In some embodiments, the channel may extend through the particle such that its ends are both located at the surface of the particle. These channels are typically formed during synthesis of the particle by inclusion followed by removal of a channel forming reagent in the particle.

The size of the pores may depend upon the size of the particle. In certain embodiments, the pores have a diameter of less than 15 microns, less than 10 microns, less than 7.5 microns, less than 5 microns, less than 2.5 microns, less than 1 micron, less than 0.5 microns, or less than 0.1 microns. The degree of porosity in porous particles may range from greater than 0 to less than 100% of the particle volume. The degree of porosity may be less than 1%, less than 5%, less than 10%, less than 15%, less than 20%, less than 25%, less than 30%, less than 35%, less than 40%, less than 45%, or less than 50%. The degree of porosity can be determined in a number of ways. For example, the degree of porosity can be determined based on the synthesis protocol of the carriers (e.g., based on the volume of the aqueous solution or other channel-forming reagent) or by microscopic inspection of the carriers post-synthesis.

The plurality of particles may be homogeneous for one or more parameters or characteristics. A plurality that is homogeneous for a given parameter, in some instances, means that particles within the plurality deviate from each other no more than about +/−10%, preferably no more than about +/−5%, and most preferably no more than about +/−1% of a given quantitative measure of the parameter. As an example, the particles may be homogeneously porous. This means that the degree of porosity within the particles of the plurality differs by not more than +/−10% of the average porosity. In other instances, a plurality that is homogeneous means that all the particles in the plurality were treated or processed in the same manner, including for example exposure to the same agent regardless of whether every particle ultimately has all the same properties. In still other embodiments, a plurality that is homogeneous means that at least 80%, preferably at least 90%, and more preferably at least 95% of particles are identical for a given parameter.

The plurality of particles may be heterogeneous for one or more parameters or characteristics. A plurality that is heterogeneous for a given parameter, in some instances, means that particles within the plurality deviate from the average by more than about +/−10%, including more than about +/−20%. Heterogeneous particles may differ with respect to a number of parameters including their size or diameter, their shape, their composition, their surface charge, their degradation profile, whether and what type of agent is comprised by the particle, the location of such agent (e.g., on the surface or internally), the number of agents comprised by the particle, etc. The invention contemplates separate synthesis of various types of particles which are then combined in any one of a number of pre-determined ratios prior to contact with the sample. As an example, in one embodiment, the particles may be homogeneous with respect to shape (e.g., at least 95% are spherical in shape) but may be heterogeneous with respect to size, degradation profile and/or agent comprised therein.

Particle size, shape and release kinetics can also be controlled by adjusting the particle formation conditions. For example, particle formation conditions can be optimized to produce smaller or larger particles, or the overall incubation time or incubation temperature can be increased, resulting in particles which have prolonged release kinetics.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells.

To enhance delivery the particles may be incorporated, for instance, into liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFEC- TIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA). A variety of methods are available for preparing liposomes e.g., U.S. Pat. Nos. 4,186,183, 4,217,344, 4,235,871, 4,261,975, 4,485,054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradeable food based particles such as cellulose.

The carrier domain can serve several functions. As discussed above, it may be useful for targeting the product to a specific region, such as a tissue. In that instance it could include a targeting agent such as a glycoprotein, an antibody, or a binding protein.

Further, the size of the carrier domain may be adjusted based on the particular use of the pro-diagnostic reagent. For instance, the carrier domain may be designed to have a size greater than 5 nm. Particles, for instance, of greater than 5 nm are not capable of entering the urine, but rather, are cleared through the reticuloendothelial system (RES; liver, spleen, and lymph nodes). By being excluded from the removal through the kidneys any uncleaved pro-diagnostic reagent will not be detected in the urine during the analysis step. Additionally, larger particles can be useful for maintaining the particle in the blood or in a tumor site where large particles are more easily shuttled through the vasculature. In some embodiments the carrier domain is 500 microns-5 nm, 250 microns-5 nm, 100 microns-5 nm, 10 microns-5 nm, 1 micron-5 nm, 100 nm-5 nm, 100 nm-10 nm, 50 nm-10 nm or any integer size range therebetween. In other instances the carrier domain is smaller than 5 nm in size. In such instance the pro-diagnostic reagent will be cleared into the urine. However, the presence of free signature molecule can still be detected for instance using mass spectrometry. In some embodiments the carrier domain is 1-5 nm, 2-5 nm, 3-5 nm, or 4-5 nm.

Optionally the carrier domain may include a biological agent. In one embodiment a biological agent could be incorporated in the carrier domain or it may make up the carrier domain. For instance, it may form the scaffold or platform that the proteolytic domain is attached to. Thus the compositions of the invention can achieve two purposes at the same time, the diagnostic methods and delivery of a therapeutic agent. In some embodiments the biological agent may be a enzyme inhibitor. In that instance the biological agent can inhibit proteolytic activity at a local site and the signature molecule can be used to test the activity of that particular therapeutic at the site of action. HIV is an example of the disease in which active proteases can be monitored. In this embodiment the composition may include a microparticle or other delivery device carrying a protease inhibitor. The protease susceptible site may be sensitive to the HIV proteases such that feedback can be provided regarding the activity of the particular protease inhibitor.

Biological agents include diagnostic, cosmetic, and therapeutic agents, such as releasable drugs. Thus, any biological agent can be incorporated within the particles, which can locally or systemically deliver or maintain the incorporated agents following administration or application to a subject. Any biocompatible or pharmacologically acceptable material can be incorporated into the particles or trapped in the pores of the particles using technology known to those skilled in the art. Biological agents include but are not limited to synthetic inorganic and organic compounds, proteins and peptides, polysaccharides and other sugars, lipids, and DNA and RNA nucleic acid sequences having therapeutic, prophylactic, cosmetic or diagnostic activities. Nucleic acid sequences include genes, plasmids, vectors, antisense molecules that bind to complementary DNA to inhibit transcription, siRNA, shRNA, and ribozymes.

In certain instances, the biological agent is an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to antibacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts.

Growth factors may also be incorporated into the carrier. As used herein, the term growth factor refers to any agent that stimulates cellular proliferation and/or differentiation. Growth factors include but are not limited to fibroblast growth factor (FGF), platelet-derived growth factor (PDGF), insulin-like growth factors (IGF) I and II, TGF-β, TGF-α, bone morphogenetic protein (BMP) (e.g., BMP-2, BMP-3, BMP-4, BMP-6, or BMP-7), hedgehog proteins, growth differentiation factors, hematopoietic colony-stimulating factors (CSF), vascular endothelium growth factor (VEGF), osteoid-inducing factor (OIF), angiogenins, endothelins, hepatocyte growth factor, keratinocyte growth factor, ADMP-1, interleukins (IL) (e.g., IL-3 and IL-6), epithelial growth factors, dexamethasone, leptin, sortilin, transglutaminase, prostaglandin E, 1,25-dihydroxyvitamin D3, ascorbic acid, pro-collagen, glycerol phosphate, TAK-778, statins, growth hormone, steel factor (SF), activin A (ACT), retinoic acid (RA), epidermal growth factor (EGF), hematopoietic growth factors, peptide growth factors, erythropoietin, tumor necrosis factors (TNF), interferons (IFN), heparin binding growth factor (HBGF), nerve growth factor (NGF) and muscle morphogenic factor (MMP).

The biological agent may also be an anti-cancer therapy. Anti-cancer therapies include for instance, radiotherapy, chemotherapy, adjuvant therapy, or any combination of the aforementioned.

The carrier domain may also be configured such that it can be detected in the body during the analysis. For instance, iron oxide can be incorporated into the particles so that the pro-diagnostic reagent can be tracked using MRI to provide non-invasive imaging data.

The carrier is linked to the signature producing domain. A signature producing domain, as used herein, is the portion of the modular structure that promotes the enzymatic reaction in the subject, causing the release of a signature molecule. The signature producing domain is either an active signature producing agent or an enzyme susceptible domain linked to a signature molecule. An active signature producing agent is a molecule that causes the formation of a signature molecule by modifying an endogenous molecule, referred to herein as a biological predictor molecule. For example the active signature producing agent is an enzyme that causes production of a signature molecule when it acts on an endogenous substrate. Enzymes include, for instance, proteases and glycosidases. The biological predictor molecule is the endogenous molecule acted upon by the active signature producing agent. Biological predictor molecules include for instance, substrates.

The enzyme susceptible site is dependent on enzymes that are active in a specific disease state. Alternatively, the enzyme specific site may be associated with enzymes that are ordinarily present but are absent in a particular disease state. For instance, tumors are associated with a specific set of enzymes. If the disease state being analyzed is a tumor then the product is designed with an enzyme susceptible site that matches that of the enzyme expressed by the tumor or other diseased tissue.

An enzyme, as used herein refers to any of numerous proteins produced in living cells that accelerate or catalyze the metabolic processes of an organism. Enzymes act on substrates. The substrate binds to the enzyme at a location called the active site just before the reaction catalyzed by the enzyme takes place. Enzymes include but are not limited to proteases, glycosidases, lipases, heparinases, phosphatases.

The enzyme susceptible site may be optimized to provide both high catalytic activity (or other enzymatic activity) for specified target enzymes but to also release optimized signature molecules for detection. For the specific detection modality of mass spectrometry, inclusion of tags for rapid affinity purification, specific charges in the sequence to increase ionization efficiency, mass defects to eliminate endogenous organic background, and unique mass signatures can improve detection. In addition to improving detection sensitivity, by programming the mass of these molecules, mass selection techniques can be harnessed to remove background during detection and focus on expected signature masses.

Patient outcome depends on the phenotype of individual diseases at the molecular level, and this is often reflected in expression of enzymes. The recent explosion of bioinformatics has facilitated exploration of complex patterns of gene expression in human tissues (Fodor, S. A. Massively parallel genomics. Science 277, 393-395 (1997)). Sophisticated computer algorithms have been recently developed capable of molecular diagnosis of tumors using the immense data sets generated by expression profiling (Khan J, Wei J S, Ringner M, Saal L H, Ladanyi M, Westermann F, et al. Classification and diagnostic prediction of cancers using gene expression profiling and artificial neural networks. Nat Med 2001; 7:673-679.). This information can be accessed in order to identify enzymes and substrates associated with specific diseases. Based on this information the skilled artisan can identify appropriate enzyme or substrates to incorporate into the pro-diagnostic reagent. Table 1 provides a non-limiting list of enzymes associated with (either increased or decreased with respect to normal) disease and in some instances, the specific substrate. Table 2 provides a non-limiting list of substrates associated with disease or other conditions. Numerous other enzyme/substrate combinations associated with specific diseases or conditions are known to the skilled artisan and are useful according to the invention.

TABLE 1

| DISEASE | ENZYME | SUBSTRATE |
| --- | --- | --- |
| Cancer | MMP | collagens, gelatin, various ECM proteins |
| Cancer | MMP-2 | type IV collagen and gelatin |
| Cancer | MMP-9 | type IV and V collagens and gelatin |
| Cancer | kallikreins | kininogens, plasminogen |
| Cancer | cathepsins | broad spectrum of substrates |
| Cancer | plasminogen activator, tPA | Plasminogen |
| Cancer | ADAM (A Diseintegrin And Metalloprotease, also MDC, Adamalysin) | various extracellular domains of transmembrane proteins |
| Pancreatic carcinoma | MMP-7 | various, e.g. collagen 18, FasL, HLE, DCN, IGFBP-3, MAG, plasminogen, other MMPs |
| Pancreatic Cancer | ADAM9, ADAM15 | various extracellular domains of transmembrane proteins |
| Prostate adenocarcinoma | Matriptase, a type II transmembrane serine protease | unspecific, cleaves after Lys or Arg residues |
| Prostate cancer | Kallikrein 3 | kininogens, plasminogen |
| Prostate cancer | ADAM15 | various extracellular domains of transmembrane proteins |
| Ovarian carcinoma | Kallikrein 6 | kininogens, plasminogen |
| Epithelial-derived tumors (breast, prostate, ovarian, colon, oral) | Matriptase, a type II transmembrane serine protease | unspecific, cleaves after Lys or Arg residues |
| Ovarian Cancer | MMP-2, MMP-9, kallikrein-10 (hk-10) | type IV and V collagens and gelatin, kininogens, plasminogen |
| Breast, gastric, prostate cancer | cathepsins B, L and D | broad spectrum of substrates |
| Endometrial cancer | cathepsin B | unspecific cleavage of a broad spectrum of substrates without clear sequence specificity |
| esophageal adenocarcinoma | cathepsin B | unspecific cleavage of a broad spectrum of substrates without clear sequence specificity |
| Invasive cancers, metastases | type II integral serine proteases (dipeptidyl peptidase IV (DPP4/CD26), seprase/fibroblast activation protein alpha (FAPalpha) and related type II transmembrane prolyl serine peptidases)) | |
| Invasive cancers, metastases viral infections | Seprase | various ECM proteins |
| All Retroviruses | viral protease | precursor GagPol fusion |
| HIV | HIV protease (HIV PR, an aspartic protease) | precursor Gag and GagPol proteins |
| Hepatitis C | NS3 serine protease | viral precursor polyprotein |
| Dengue | Dengue protease | auocleavage (NS2B/NS3), NS3/NS4A and NS4B/NS5 cleavage |
| West Nile bacterial infections | NS2B/NS3pro | viral precursor polyprotein |
| *Legionella* spp. | zinc metalloprotease | Me-Arg-Pro-Tyr |
| Meninogencephalitis | histolytic cysteine protease | |
| *Streptococcus pyogenes* (Group A *Streptococcus*) | streptococcal pyrogenic exotoxin B (SpeB) | extracellular matrix, immunoglobulins, complement components |
| *Chlostridium difficile* | Cwp84 | fibronectin, laminin, vitronectin and other ECM proteins |
| Alzheimer's disease | BACE-1,2 (Alzheimer secretase) | β-amyloid precursor protein |
| Stroke and recovery | MMP, tPA | |
| cardiovascular disease | Angiotensin Converting Enzyme (ACE) | angiotensin I, bradykinin |
| Atherosclerosis | cathepsin K, L, S | broad spectrum of substrates |
| arthritis | MMP-1 | triple-helical fibrillar collagens |
| rheumatoid arthritis | thrombin | Osteopontin |
| osteoarthritis | thrombin | Osteopontin |
| osteoporosis/osteoarthritis | cathepsin K, S | broad spectrum of substrates |
| Arthritis, inflammatory joint disease | Aggrecanase (ADAMTS4, ADAMTS11) | aggrecans (proteoglycans) |

TABLE 1-continued

| DISEASE | ENZYME | SUBSTRATE |
| --- | --- | --- |
| thrombosis | factor Xa (thrombokinase) | Prothrombin |
| thrombosis | ADAMTS13 | von Willebrand factor (vWF) |
| thrombosis | plasminogen activator, tPA | Plasminogen |
| Stress-induced Renal pressure natriuresis | Prostasin | epithelial Na channel subunits |

TABLE 2

| DISEASE | TARGET SUBSTRATE | ENZYME |
| --- | --- | --- |
| Inflammation | Interleukin 1 beta | MMP-2, MMP-3, MMP-9, Trypsin, chymotrypsin, pepsin, Lys-C, Glu-C, Asp-N, Arg-C |
| Pituitary gland dysfunction, abnormal bone density, growth disorders | IGFBP-3 | MMP-1, MMP-3, MMP-9, Trypsin, chymotrypsin, pepsin, Lys-C, Glu-C, Asp-N, Arg-C |
| Cancer | TGF-beta | MMP-9, Trypsin, chymotrypsin, pepsin, Lys-C, Glu-C, Asp-N, Arg-C |
| Cancer, autoimmune disease | TNF | MMP-7, Trypsin, chymotrypsin, pepsin, Lys-C, Glu-C, Asp-N, Arg-C |
| Cancer, autoimmune disease | FASL | MMP-7, Trypsin, chymotrypsin, pepsin, Lys-C, Glu-C, Asp-N, Arg-C |
| Wound healing, cardiac disease | HB-EGF | MMP-3, Trypsin, chymotrypsin, pepsin, Lys-C, Glu-C, Asp-N, Arg-C |
| Pfeiffer syndrome | FGFR1 | MMP-2, Trypsin, chymotrypsin, pepsin, Lys-C, Glu-C, Asp-N, Arg-C |
| Cancer | Decorin | MMP-2, MMP-3, MMP-7, Trypsin, chymotrypsin, pepsin, Lys-C, Glu-C, Asp-N, Arg-C |
| Cancer | Tumor associated carbohydrate antigens | Endoglycosidases |
| Cancer | Sialyl Lewis$^a$ | O-glycanase |
| Cancer | Sialyl Lewis$^X$ | O-glycanase |
| Cancer/Rheumatoid Arthritis, pulmonary hypertension | VEGF | Trypsin, chymotrypsin, pepsin, Lys-C, Glu-C, Asp-N, Arg-C |
| Cancer | EGF | Trypsin, chymotrypsin, pepsin, Lys-C, Glu-C, Asp-N, Arg-C |
| Cancer | IL2 | Trypsin, chymotrypsin, pepsin, Lys-C, Glu-C, Asp-N, Arg-C |
| Cancer inflammation/angiogenesis | IL6 | Trypsin, chymotrypsin, pepsin, Lys-C, Glu-C, Asp-N, Arg-C |
| Cancer | IFN-γ | Trypsin, chymotrypsin, pepsin, Lys-C, Glu-C, Asp-N, Arg-C |
| Cancer inflammation/angiogenesis, Rheumatoid Arthritis | TNF-α | Trypsin, chymotrypsin, pepsin, Lys-C, Glu-C, Asp-N, Arg-C |
| Cancer, Pulmonary fibrosis, Asthma | TGF-β | Trypsin, chymotrypsin, pepsin, Lys-C, Glu-C, Asp-N, Arg-C |
| Cancer, Pulmonary hypertension | PDGF | Trypsin, chymotrypsin, pepsin, Lys-C, Glu-C, Asp-N, Arg-C |
| Cancer, pulmonary cystadenoma | Fibroblast growth factor (FGF) | Trypsin, chymotrypsin, pepsin, Lys-C, Glu-C, Asp-N, Arg-C |
| Cancer | Brain-derived neurotrophic factor (BDNF) | Trypsin, chymotrypsin, pepsin, Lys-C, Glu-C, Asp-N, Arg-C |
| Cancer | Interferon regulatory factors (IRF-1, IRF-2) | Trypsin, chymotrypsin, pepsin, Lys-C, Glu-C, Asp-N, Arg-C |
| Inhibitor of tumor suppressors | MIF | Trypsin, chymotrypsin, pepsin, Lys-C, Glu-C, Asp-N, Arg-C |
| Lymphomas/carcinomas, alveolar proteinosis | GM-CSF | Trypsin, chymotrypsin, pepsin, Lys-C, Glu-C, Asp-N, Arg-C |
| Cancer invasion | M-CSF | Trypsin, chymotrypsin, pepsin, Lys-C, Glu-C, Asp-N, Arg-C |
| Chemical carcinogenesis, multiple schlerosis, rheumatoid arthritis, Crohn's disease | IL-12 | Trypsin, chymotrypsin, pepsin, Lys-C, Glu-C, Asp-N, Arg-C |

TABLE 2-continued

| DISEASE | TARGET SUBSTRATE | ENZYME |
| --- | --- | --- |
| Natural Killer T cell leukemias, inflammatory bowel disease, rheumatoid arthritis | IL-15 | Trypsin, chymotrypsin, pepsin, Lys-C, Glu-C, Asp-N, Arg-C |
| Cirrhosis | Tissue inhibitor of MMPs (TIMPs) | Trypsin, chymotrypsin, pepsin, Lys-C, Glu-C, Asp-N, Arg-C |
| Cirrhosis | Collagen I, III | MMP-1, MMP-8, Trypsin, chymotrypsin, pepsin, Lys-C, Glu-C, Asp-N, Arg-C |
| Cirrhosis | Collagen IV, V | MMP-2, Trypsin, chymotrypsin, pepsin, Lys-C, Glu-C, Asp-N, Arg-C |

Several of the enzyme/substrates described above are described in the following publications, all of which are incorporated herein in their entirety by reference: Parks, W. C. and R. P. Mecham (Eds): Matrix metalloproteinases. San Diego: Academic Press; 1998; Nagase, H. and J. F. Woessner, Jr. (1999) J. Biol. Chem. 274:21491; Ito, A. et al. (1996) J. Biol. Chem. 271:14657; Schonbeck, U. et al. (1998) J. Immunol. 161: 3340; Rajah, R. et al. (1999) Am. J. Cell Mol. Biol. 20:199; Fowlkes, J. L. et al. (1994) Endocrinology 135:2810; Manes, S. et al. (1999) J. Biol. Chem. 274:6935; Mira, E. et al. (1999) Endocrinology 140:1657; Yu, Q. and I. Stamenkovic (2000) Genes Dev. 14:163; Haro, H. et al. (2000) J. Clin. Invest. 105:143; Powell, C. P. et al. (1999) Curr. Biol. 9:1441; Suzuki, M. et al. (1997) J. Biol. Chem. 272:31730; Levi, E. et al. (1996) Proc. Natl. Acad. Sci. USA 93:7069; Imai, K. et al. (1997) Biochem. J. 322:809; Smith, M. M. et al. (1995) J. Biol. Chem. 270:6440; and Dranoff, G. (2004) Nat. Rev. Cancer 4: 11-22.

The signature producing domain may be attached directly to the carrier. For instance it may be coated directly on the surface of microparticles using known techniques. Alternatively if the carrier is a protein material it may be directly connected through a peptide bond. Additionally, the signature producing domain may be connected to the carrier domain through the use of a linker. As used herein "linked" or "linkage" means two entities are bound to one another by any physicochemical means. Any linkage known to those of ordinary skill in the art, covalent or non-covalent, is embraced. Thus, in some embodiments the carrier has a linker attached to an external surface, which can be used to link the signature producing domain. Another molecule can also be attached to the linker.

The signature producing domain is preferably a polymer made up of a plurality of chemical units. A "chemical unit" as used herein is a building block or monomer which may be linked directly or indirectly to other building blocks or monomers to form a polymer. In some embodiments the signature producing domain is a peptide that is susceptible to cleavage by an enzyme or causes cleavage of a substrate associated with a disease or condition. A number of examples of when the proteolytic cleavage site is a peptide are presented in the table above.

The enzyme susceptible domain may also be a polysaccharide. Some polysaccharide specific degrading enzymes are associated with tumors, angiogenesis and other conditions. A "polysaccharide" is a biopolymer comprised of linked saccharide or sugar units. The polysaccharides used as proteolytic susceptible domains may be isolated or synthesized de novo. For example, the polysaccharides may be isolated from natural sources e.g. purified, as by cleavage and gel separation or may be synthesized e.g., by chemical synthesis and incorporated into the pro-diagnostic reagent.

For instance, HSGAG degrading enzymes are enzymes that can be analyzed according to the methods of the invention. HSGAG degrading enzymes include heparinase-I, heparinase-II, heparinase-III, D-glucuronidase and L-iduronidase. The heparinases cleave at the glycosidic linkage before a uronic acid. Heparinase I clips at a glycosidic linkage before a 2-O sulfated iduronic acid. Heparinase-III cleaves at a glycosidic linkage before an unsulfated glucuronic acid. Heparinase-II cleaves at both Hep-I and Hep-III cleavable sites. Glucuronidase and iduronidase, as their name suggests cleave at the glycosidic linkage after a glucuronic acid and iduronic acid respectively. Nitrous acid clips randomly at glycosidic linkages after a N-sulfated hexosamine and converts the six membered hexosamine ring to a 5 membered anhydromannitol ring. Appropriate enzyme susceptible domains may be designed based on the known substrates and cleavage sites of these enzymes.

The pro-diagnostic reagent may also include an implantable microdelivery device that houses the modular structure. An implantable microdelivery device is any type of device, that is sized for implantation into a body and can retain the modular structure. For instance the device may be an implantable capsule that contains the modular structure housed there in. The capsule may have a semi-permeable membrane, such that the modular structure cannot pass though the membrane, but which is permeable to endogenous molecules such as enzymes and substrates as well as signature molecules. Alternatively the implantable microdelivery device may be a chip having the modular structure attached thereto. Examples of implantable microdelivery devices include but are not limited to implantable capsules, chips, sustained-release formulations, multi-pulse drug delivery resorbable polymeric microchip device (Grayson et al. Nature Materials, VOL 2, November 2003, p. 767), and controlled release microchips (Santini et al Nature, vol 397, 1999, p. 335). These devices may be made from many materials include many of the polymeric materials described herein. Preferably the implantable devices are biocompatible and non-toxic.

Modification of the enzyme susceptible domain by an enzyme in vivo, results in the production of a signature molecule. Alternatively, when the signature producing domain is an enzyme the enzyme cleaves an endogenous substrate producing a signature molecule from the endogenous substrate. The signature molecule is a detectable molecule. It can be part of the enzyme susceptible domain, e.g. the piece that is released or added upon cleavage or it can be a separate entity. The signature molecule may be, for instance, a peptide, nucleic acid, small molecule, fluorophore/quencher, carbohydrate, particle, radiolabel, MRI-active compound, inorganic material, organic material, with encoded characteristics to facilitate optimal detection.

The signature molecule may be detected by any known detection methods. A variety of methods may be used, depending on the nature of the signature molecule/label. Labels on signature molecules may be directly detected through optical or electron density, radioactive emissions, nonradiative energy transfers, or signature molecules may be indirectly detected with antibody conjugates, strepavidin-biotin conjugates, mass spectrometry, liquid chromatography-mass spectrometry, PCR analysis, DNA microarray, and fluorescence analysis.

The analysis step may be performed directly on the biological sample or the signature component may be purified to some degree first. For instance, a purification step may involve isolating the signature molecule from other components in the biological sample. Purification steps include methods such as affinity chromatography. As used herein an "isolated molecule" or "purified molecule" is a signature molecule that is isolated to some extent from its natural environment. The isolated or purified molecule need not be 100% pure or even substantially pure prior to analysis.

The methods for analysing signature molecules by identifying the presence of a signature molecule may be used to provide a qualitative assessment of the molecule (e.g., whether the signature molecule is present or absent) or a quantitative assessment (e.g., the amount of signature molecule present to indicate a comparative activity level of the enzymes. The quantitative value may be calculated by any means, such as, by determining the percent relative amount of each fraction present in the sample. Methods for making these types of calculations are known in the art.

A signature molecule can be determined using mass spectrometry. The mass spectrometry data may be a valuable tool to ascertain information about the signature molecule in the biological sample. After a molecular weight of a signature molecule is identified, it may be compared to molecular weights of other known signature molecules.

Molecular weight may be determined by several methods including mass spectrometry. The use of mass spectrometry for determining the molecular weight of molecules is well known in the art. Liquid chromatography-mass spectrometry (LC-MS, or alternatively HPLC-MS) is an analytical chemistry technique that combines the physical separation capabilities of liquid chromatography (or HPLC) with the mass analysis capabilities of mass spectrometry. LC-MS is a powerful technique which has very high sensitivity and specificity. It can be used to detect signature molecules in a complex mixture. Other types of mass spectrometry known in the art, such as, matrix-assisted laser desorption ionization mass spectrometry (MALDI-MS), electron spray-MS, fast atom bombardment mass spectrometry (FAB-MS) and collision-activated dissociation mass spectrometry (CAD) can also be used to identify the molecular weight of the signature molecule.

Methods for performing mass spectrometry using nucleic acid samples have been described. See e.g., U.S. Pat. No. 5,885,775. U.S. Pat. Nos. 7,412,332 and 6,597,996 describe methods for detecting polysaccharide molecules using mass spectrometry. As shown in these patent applications, one technique for comparing molecular weights is to generate a mass line and compare the molecular weight of the unknown polysaccharide to the mass line to determine a subpopulation of polysaccharides which have the same molecular weight. A "mass line" is an information database, preferably in the form of a graph or chart which stores information for each possible type of polysaccharide having a unique sequence based on the molecular weight of the polysaccharide. Because mass spectrometry data indicates the mass of a fragment to 1 Da accuracy, a length may be assigned uniquely to a fragment by looking up a mass on the mass line.

NMR spectroscopy is an analytical tool that allows for the determination of molecular structure. Utilizing the magnetic properties of some nuclei, the nuclear spins of the nuclei can be oriented randomly with an external magnetic field. Oriented nuclei that are subsequently irradiated at the correct frequency will absorb energy and transition to a higher energy state. Upon relaxation this energy is emitted and detected in various NMR systems. This irradiation of the nuclei occur in pulses. In basic one dimensional (1D) NMR the excitation is produced from a single pulse and emitted radiation is detected as free induction decay (FID). In two dimensional (2D) NMR spectroscopy the nuclei is irradiated with two pulses, and acquisition of the FID occurs at many time points with a delay between the pulses.

When the signature molecule is a nucleic acid, it can also be analyzed using PCR and microarrays. PCR methods are well-known in the art. For instance, U.S. Pat. No. 5,333,675, issued to Mullis et al. describes an apparatus and method for performing automated PCR. In general, performance of a PCR method results in amplification of a selected region of DNA by providing two DNA primers, each of which is complementary to a portion of one strand within the selected region of DNA. The primer is hybridized to a template strand of nucleic acid in the presence of deoxyribonucleotide triphosphates (dATP, dCTP, dGTP, and dTTP) and a chain extender enzyme, such as DNA polymerase. The primers are hybridized with the separated strands, forming DNA molecules that are single stranded except for the region hybridized with the primer, where they are double stranded. The double stranded regions are extended by the action of the chain extender enzyme (e.g. DNA polymerase) to form an extended double stranded molecule between the original two primers. The double stranded DNA molecules are separated to produce single strands which can then be re-hybridized with the primers. The process is repeated for a number of cycles to generate a series of DNA strands having the same nucleotide sequence between and including the primers.

Chain extender enzymes are well known in the art and include, for example, *E. coli* DNA polymerase I, klenow fragment of *E. coli* DNA polymerase I, T4 DNA polymerase, T7 DNA polymerase, recombinant modified T7 DNA polymerase, reverse transcriptase, and other enzymes. Heat stable enzymes are particularly preferred as they are useful in automated thermal cycle equipment. Heat stable polymerases include, for example, DNA polymerases isolated from *Bacillus stearothermophilus* (Bio-Rad), *Thermus thermophilous* (finzyme, ATCC number 27634), *Thermus* species (ATCC number 31674), *Thermus aquaticus* strain TV11518 (ATCC number 25105), *Sulfolobus acidocaldarius*, described by Bukhrashuili et al., *Biochem. Biophys. Acta.*, 1008:102-07 (1909), *Thermus filiformus* (ATCC number 43280), Taq DNA polymerase, commercially available from Perkin-Elmer-Cetus (Norwalk, Conn.), Promega (Madison, Wis.) and Stratagene (La Jolla, Calif.), and AmpliTaq™ DNA polymerase, a recombinant *Thermus equitus* Taq DNA polymerase, available from Perkin-Elmer-Cetus and described in U.S. Pat. No. 4,889,818.

Preferably, the PCR-based methods performed according to the invention are automated and performed using thermal cyclers. Many types of thermal cyclers are well-known in the art. For instance, M.J. Research (Watertown, Mass.) provides a thermal cycler having a peltier heat pump to provide precise uniform temperature control in the thermal cyclers; DeltaCycler thermal cyclers from Ericomp (San Diego, Calif.) also are peltier-based and include automatic ramping control, time/temperature extension programming and a choice of tube or microplate configurations. The RoboCycler™ by Stratagene (La Jolla, Calif.) incorporates robotics to produce rapid temperature transitions during cycling and well-to-well uniformity between samples; and a particularly preferred cycler, is the Perkin-Elmer Applied Biosystems (Foster City, Calif.) ABI Prism™ 877 Integrated Thermal cycler, which is operated through a programmable interface that automates liquid handling and thermocycling processes for fluorescent DNA sequencing and PCR reactions.

The presence or absence of enzymes in the subject may also be determined using hybridization techniques. Standard hybridization techniques of microarray technology are utilized to assess the presence of nucleic acids in the biological sample. Microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

According to the present invention, microarray substrates may include but are not limited to glass, silica, aluminosilicates, borosilicates, metal oxides such as alumina and nickel oxide, various clays, nitrocellulose, or nylon. In all embodiments a glass substrate is preferred. An "array" as used herein is a set of molecules arranged in a specific order with respect to a surface. Preferably the array is composed of polynucleotides attached to the surface. Oligonucleotide arrays can be used to screen nucleic acid samples for a target nucleic acid, which can be labeled with a detectable marker. A fluorescent signal resulting from hybridization between a target nucleic acid and a substrate-bound oligonucleotide provides information relating to the identity of the target nucleic acid by reference to the location of the oligonucleotide in the array on the substrate. Such a hybridization assay can generate thousands of signals which exhibit different signal strengths. These signals correspond to particular oligonucleotides of the array. Different signal strengths will arise based on the amount of labeled target nucleic acid hybridized with an oligonucleotide of the array.

Conditions for optimal hybridization are known. The hybridization conditions in general are those used commonly in the art, such as those described in Sambrook et al., "Molecular Cloning: A Laboratory Manual", (1989), 2nd Ed., Cold Spring Harbor, N.Y.; Berger and Kimmel, "Guide to Molecular Cloning Techniques", *Methods in Enzymology*, (1987), Volume 152, Academic Press, Inc., San Diego, Calif.; and Young and Davis, (1983), *PNAS* (USA) 80:1194. In general, incubation temperatures for hybridization of nucleic acids range from about 20° C. to 75° C. For probes 17 nucleotides residues and longer, a preferred temperature range for hybridization is from about 50° C. to 54° C. The hybridization temperature for longer probes is preferably from about 55° C. to 65° C. and for shorter probes is less than 52° C. Rehybridization may be performed in a variety of time frames. Preferably, hybridization of SNP and RCGs performed for at least 30 minutes.

The signature molecule may be labeled. For example, a label may be added directly to a nucleic acid when the isolated signature molecule is subjected to PCR. For instance, a PCR reaction performed using labeled primers or labeled nucleotides will produce a labeled product. Labeled nucleotides (e.g., fluorescein-labeled CTP) are commercially available. Methods for attaching labels to nucleic acids are well known to those of ordinary skill in the art and, in addition to the PCR method, include, for example, nick translation and end-labeling.

Labels suitable for use in the methods of the present invention include any type of label detectable by standard means, including spectroscopic, photochemical, biochemical, electrical, optical, or chemical methods. Preferred types of labels include fluorescent labels such as fluorescein. A fluorescent label is a compound comprising at least one fluorophore. Commercially available fluorescent labels include, for example, fluorescein phosphoramidides such as fluoreprime (Pharmacia, Piscataway, N.J.), fluoredite (Millipore, Bedford, Mass.), FAM (ABI, Foster City, Calif.), rhodamine, polymethadine dye derivative, phosphores, Texas red, green fluorescent protein, CY3, and CY5. Polynucleotides can be labeled with one or more spectrally distinct fluorescent labels. "Spectrally distinct" fluorescent labels are labels which can be distinguished from one another based on one or more of their characteristic absorption spectra, emission spectra, fluorescent lifetimes, or the like. Spectrally distinct fluorescent labels have the advantage that they may be used in combination ("multiplexed"). Radionuclides such as $^{3}H$, $^{125}I$, $^{35}S$, $^{14}C$, or $^{32}P$ are also useful labels according to the methods of the invention. A plurality of radioactively distinguishable radionuclides can be used. Such radionuclides can be distinguished, for example, based on the type of radiation (e.g. $\alpha$, $\beta$, or $\delta$ radiation) emitted by the radionuclides. The $^{32}P$ signal can be detected using a phosphoimager, which currently has a resolution of approximately 50 microns. Other known techniques, such as chemiluminescence or colormetric (enzymatic color reaction), can also be used.

Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET). Cleavage of the peptide results in separation of the chromophore and fluorophore, removal of the quench, and generation of a subsequent signal measured from the donor fluorophore.

Once the data is obtained, e.g. as a two-dimensional image, a computer can be used to transform the data into a displayed image which varies in color depending on the intensity of light emission at a particular location. Any type of commercial software which can perform this type of data analysis can be used. In general, the data analysis involves the steps of determining the intensity of the fluorescence emitted as a function of the position on the substrate, removing the outliers, and calculating the relative binding affinity. One or more of the presence, absence, and intensity of signal corresponding to a label is used to assess the presence or absence of an signature molecule. The presence and absence of one or more signature molecules can be used to determine the disease status of an individual based on the presence or absence of an enzyme.

The data may also be observed and analyzed manually. For instance, the presence or absence of a fluorescent label may be observed in order to provide the diagnostic or prognostic information from the data.

The disease or condition assessed according to the methods of the invention is any disease or condition that is associated with an enzyme. For instance, cancer, cardiovascular disease, arthritis, viral, bacterial, parasitic or fungal infection, Alzheimer's disease emphysema, thrombosis, hemophilia, stroke, organ disfunction, any inflammatory condition, vascular disease, parenchymal disease, or a pharmacologically-induced state are all known to be associated with enzymes. A pharmacologically induced state is a condition in which enzyme inhibitors and other agents directly or indirectly affect enzyme activities. Thus each of the these can be assessed or monitored or studied according to methods of the invention.

It is useful to be able to differentiate non-metastatic primary tumors from metastatic tumors, because metastasis is a major cause of treatment failure in cancer patients. If metastasis can be detected early, it can be treated aggressively in order to slow the progression of the disease. Metastasis is a complex process involving detachment of cells from a primary tumor, movement of the cells through the circulation, and eventual colonization of tumor cells at local or distant tissue sites. Additionally, it is desirable to be able to detect a predisposition for development of a particular cancer such that monitoring and early treatment may be initiated. For instance, an extensive cytogenetic analysis of hematologic malignancies such as lymphomas and leukemias have been described, see e.g., Solomon et al., Science 254, 1153-1160, 1991. Early detection or monitoring using the non-invasive methods of the invention may be useful.

Solid tumors progress from tumorigenesis through a metastatic stage and into a stage at which several different active proteases can be involved. Some protease are believed to alter the tumor such that it can progress to the next stage, i.e., by conferring proliferative advantages, the ability to develop drug resistance or enhanced angiogenesis, proteolysis, or metastatic capacity.

Alzheimer's disease causes progressive dementia with consequent formation of amyloid plaques, neurofibrillary tangles, gliosis and neuronal loss. The disease occurs in both genetic and sporadic forms whose clinical course and pathological features are quite similar. Three genes have been discovered to date which, when mutated, cause an autosomal dominant form of Alzheimer's disease. These encode the amyloid protein precursor (APP) and two related proteins, presenilin-1 (PS1) and presenilin-2 (PS2). Mutations in any of the three proteins have been observed to enhance proteolytic processing of APP via an intracellular pathway that produces amyloid beta peptide (Aβ peptide), a 40-42 amino acid long peptide that is the primary component of amyloid plaque in Alzheimer's disease. Pathological processing of APP at the β- and γ-secretase sites, which are located N-terminal and C-terminal to the α-secretase site, respectively, produces a very different result than processing at the α site. Sequential processing at the β- and γ-secretase sites releases the Aβ peptide, a peptide possibly very important in Alzheimer's disease pathogenesis. The β secretase enzyme, termed Aspartyl Protease 2 (Asp2) is thought to mediate this processing. The presence of Asp2 activity is important for the diagnosis and prognosis of Alzheimer's disease. This enzyme and it's substrate can also be used in the methods of the invention to monitor the ability of a therapeutic to function in slowing the progression of Alzheimer's disease.

As used herein, a subject is a human, non-human primate, cow, horse, pig, sheep, goat, dog, cat, or rodent. In all embodiments human subjects are preferred. In aspects of the invention pertaining to cancer diagnosis in general the subject preferably is a human suspected of having cancer, or a human having been previously diagnosed as having cancer. Methods for identifying subjects suspected of having cancer may include physical examination, subject's family medical history, subject's medical history, biopsy, or a number of imaging technologies such as ultrasonography, computed tomography, magnetic resonance imaging, magnetic resonance spectroscopy, or positron emission tomography.

As used herein, a biological sample is a tissue sample. The biological sample may be examined in the body, for instance, by detecting a label at the site of the tissue, i.e. urine. Alternatively the biological sample may be collected from the subject and examined in vitro. Biological samples include but are not limited to urine, blood, saliva, or mucous secretion. In preferred embodiments the tissue sample is obtained non-invasively, such as the urine.

A "plurality" of elements, as used throughout the application refers to 2 or more of the elements.

The pro-diagnostic reagents of the invention are administered to the subject in an effective amount for detecting enzyme activity. An "effective amount", for instance, is an amount necessary or sufficient to cause release of a detectable level of signature molecule in the presence of an enzyme. In some instances when a therapeutic is administered in the pro-diagnostic reagent, the effective amount is that amount necessary to realize a desired biologic effect. An "effective amount for treating Alzheimer's disease", for instance, could be that amount necessary to (i) prevent further memory loss and/or (ii) arresting or slowing memory loss with respect to memory loss in the absence of the therapy. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of symptoms resulting from the disease. In another embodiment, the biological effect is the complete abrogation of the disease, as evidenced for example, by the absence of a symptom of the disease.

The effective amount of a compound of the invention described herein may vary depending upon the specific compound used, the mode of delivery of the compound, and whether it is used alone or in combination. The effective amount for any particular application can also vary depending on such factors as the disease being assessed or treated, the particular compound being administered, the size of the subject, or the severity of the disease or condition as well as the detection method. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective regimen can be planned.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The agent may comprise different types of carriers depending on whether it is to be administered in solid, liquid or aerosol form, and whether it need to be sterile for such routes of administration as injection.

Preferably the material is injected into the body but could also be administered by other routes. For instance, the compounds of the present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

According to the methods of the invention, the compound may be administered in a pharmaceutical composition. In general, a pharmaceutical composition comprises the compound of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The data generated according to the invention may optionally be converted into a bar code or other human- or machine-readable form. For example, each line of a bar code may indicate the presence or absence of a specific enzyme or groups of specific enzymes for a particular subject. The bar code data can be compared with a database of information on other subjects or information on the disease to aid in the diagnosis, prognosis or other analysis of the test subject.

In one embodiment of the invention, the data generated herein is used to select clinical treatment paradigms for cancers. Treatment options, as described herein, may include but are not limited to: radiotherapy, chemotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment paradigm based on evaluation of data generated by the methods described herein.

In certain embodiments, software for calculating and processing the data as described herein can be provided on a computer connected by data link to a data generating device, such as a mass spectrometer, microarray reader or PCR machine. Any standard data link can be used, including serial or parallel cables, radio frequency or infrared telemetry links, LAN connections, WAN connections, etc. Alternatively, data can be transferred by computer-readable medium (e.g., magnetic or optical medium) and read by the software. The data also can be entered directly by the user via user interface, such as a keyboard, monitor, mouse, graphical user interface such as touch screen, etc. The computer may be contained within the data generating device, providing an integrated system for generating raw data, calculating ratios, and displaying such ratios. One or more computers also may be linked to one or more data generating devices and one or more display devices, such as in a local area network or wide area network.

In one embodiment of the invention, a visual display is used to display the data for the classification, diagnosis, prediction of prognosis and/or therapeutic monitoring. The visual display can be a graphical user interface, such as a monitor, or a printer.

The data can be processed individually or by a computer. For instance, a computer-implemented method for generating a data structure, tangibly embodied in a computer-readable medium, representing a quantitative value of a set of signature molecules may be performed according to the invention. The quantitative values may be compared with a reference database. Alternatively a qualitative pattern may be compared with a reference database.

A computer system that may implement the above as a computer program typically may include a main unit connected to both an output device which displays information to a user and an input device which receives input from a user. The main unit generally includes a processor connected to a memory system via an interconnection mechanism. The input device and output device also may be connected to the processor and memory system via the interconnection mechanism.

One or more output devices may be connected to the computer system. Example output devices include a cathode ray tube (CRT) display, liquid crystal displays (LCD), printers, communication devices such as a modem, and audio output. One or more input devices also may be connected to the computer system. Example input devices include a keyboard, keypad, track ball, mouse, pen and tablet, communication device, and data input devices such as sensors. The subject matter disclosed herein is not limited to the particular input or output devices used in combination with the computer system or to those described herein.

The computer system may be a general purpose computer system which is programmable using a computer programming language, such as C++, Java, or other language, such as a scripting language or assembly language. The computer system also may include specially-programmed, special purpose hardware such as, for example, an Application-Specific Integrated Circuit (ASIC). In a general purpose computer system, the processor typically is a commercially-available processor, of which the series x86, Celeron, and Pentium processors, available from Intel, and similar devices from AMD and Cyrix, the 680X0 series microprocessors available from Motorola, the PowerPC microprocessor from IBM and the Alpha-series processors from Digital Equipment Corporation, are examples. Many other processors are available. Such a microprocessor executes a program called an operating system, of which Windows NT, Linux, UNIX, DOS, VMS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages may be written.

A memory system typically includes a computer readable and writeable nonvolatile recording medium, of which a magnetic disk, a flash memory and tape are examples. The disk may be removable, such as a "floppy disk," or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element typically allows for faster access to the information by the processor than does the disk. The processor generally manipulates the data within the integrated circuit memory and then copies the data to the disk after processing is completed. A variety of mechanisms are known for managing data movement between the disk and the integrated circuit memory element, and the subject matter disclosed herein is not limited to such mechanisms. Further, the subject matter disclosed herein is not limited to a particular memory system.

The subject matter disclosed herein is not limited to a particular computer platform, particular processor, or particular high-level programming language. Additionally, the computer system may be a multiprocessor computer system or may include multiple computers connected over a computer network. It should be understood that each module may be separate modules of a computer program, or may be separate computer programs. Such modules may be operable on separate computers. Data may be stored in a memory system or transmitted between computer systems. The subject matter disclosed herein is not limited to any particular implementation using software or hardware or firmware, or any combination thereof. The various elements of the system, either individually or in combination, may be implemented as a computer program product tangibly embodied in a machine-readable storage device for execution by a computer processor. Various steps of the process may be performed by a computer processor executing a program tangibly embodied on a computer-readable medium to perform functions by operating on input and generating output. Computer programming languages suitable for implementing such a system include procedural programming languages, object-oriented programming languages, and combinations of the two.

The invention further provides efficient methods of identifying pharmacological agents or lead compounds for agents active in vivo. Generally, the screening methods involve assaying for compounds that beneficially alter enzyme activity in vivo. Such methods according to the invention are adaptable to automated, high-throughput screening of compounds.

The methods may be used in any subject. For instance animal models of disease may be used to screen multiple putative therapeutic agents in order to assess the activity level of the putative therapeutic agents on particular enzymes associated with disease. For instance, a library of pro-diagnostic reagents having different putative therapeutic agents associated with the carrier can be administered to the animal model. If each therapeutic agent is associated with a unique signature molecule, then the activity of the putative therapeutic agent could be assessed by analyzing the level of signature molecule in the urine as described herein.

Additionally, the methods may be used for the advancement of personalized medicine. For instance, a set of pro-diagnostic reagents having multiple therapeutic agents, each therapeutic agent associated with a discreet signature molecule could be administered to a subject having a disease to assess which therapeutic agent is most effective in that individual subject. Based on the data, an appropriate therapeutic strategy could be designed. An example of this may be seen in HIV. Protease inhibitors are used therapeutically to inhibit the activity of critical proteases associated with HIV survival and activity. A set of pro-diagnostic reagents could be generated having different enzyme inhibitors as the carrier or part of the carrier. Each enzyme inhibitor is associated with a particular signature molecule, such that the activity of the particular inhibitor on the enzyme can be assessed by monitoring the level of signature in the urine. For instance a particularly active inhibitor would cause a reduced level of signature molecule being transported to the urine.

Typically, a known active therapeutic agent may serves as a negative control, i.e., the known therapeutic agent is incorporated into a pro-diagnostic reagent. Putative therapeutic agents, also referred to herein as candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

The invention also includes kits having a container housing a pro-diagnostic reagent, wherein the pro-diagnostic reagent comprises a carrier domain linked to a signature producing domain. The kit may also include a second container housing an analytical reagent.

The kits, also referred to as articles, include pharmaceutical or diagnostic grade compounds of the invention in one or more containers. The article may include instructions or labels promoting or describing the use of the compounds of the invention. For instance, the kit may include instructions for administering the pro-diagnostic reagent to a subject and for analyzing the signature molecule of the pro-diagnostic reagent in a biological sample of the subject.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

In another preferred embodiment, compositions of the invention are stored in containers with biocompatible detergents, including but not limited to, lecithin, taurocholic acid, and cholesterol; or with other proteins, including but not limited to, gamma globulins and serum albumins.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention further provides an article of manufacture comprising a needle or syringe, preferably packaged in sterile form, for injection of the formulation, and/or a packaged alcohol pad.

EXAMPLES

Example 1: Methods

Syntheses of Nanoparticle Pro-Diagnostic Reagents 40 nm dextran-coated iron oxide nanoparticles (NP; 115,000 g/mole per iron core) were dissolved in 1× phosphate buffered saline (PBS; 137 mM NaCl, 10 mM Phosphate, 2.7 mM KCl, pH 7.4) at a concentration of 2 mg/mL. Vivotag-750 fluorophore was labeled on the NPs such that each NP has around 2 VT-750 fluorophores. The linker N-succinimidyl iodoacetate (SIA) was dissolved in DMSO at 20 mg/mL. The two solutions were mixed to obtain a 1-to-7 mass ratio between iron oxide NPs and SIA for 2 hr at room temperature with shaking. Size exclusion chromatography (column diameter×height=1 cm×30 cm; media: Sephadex G-50-coarse) was used to separate out the excess SIA and to exchange NPs into borate buffer (50 mM sodium borate, 5 mM EDTA, pH 8.3).

Each of the 43 fluorescein-labeled peptides; MIT Biopolymers Laboratory) was dissolved in DMSO at 25 mg/mL. Thiol polyethylene glycol (SH-PEG; MW=20 k) was dissolved in borate buffer at 1 mg/mL. Each of the 43 peptides, SH-PEGs, and the activated NPs were left to for >12 hr at molar ratio of 1:20:95=NP:SH-PEG:peptide, making 43 different peptide-PEG-NPs. Additional borate buffer was added to the reactants to bring the DMSO to <10% of the total reaction volume.

After the linkers on the NP surface had reacted with 20 k SH-PEGs and fluorophore-peptides, the five final-product solutions were filtered on centrifugal filter columns (Amicon, Millipore; MW=100 k) at 4,200 rcf to remove the un-conjugated SH-PEGs and peptides to <0.1% of the original conjugated quantity. 1×HEPES salt buffer (100 mM 4-(2-hydroxyethyl)-1-piperazine ethanesulfonic acid, 150 mM NaCl, pH 7.5) was used to replace the borate buffer and DMSO during centrifugation until <0.1% volume of borate and <0.02% volume of the DMSO were left in the samples.

The 43 newly made peptide-PEG-NPs (pP-NPs) were analyzed with a spectrometer to assess the number of peptides bound to each nanoparticle. Nanoparticle spectra were normalized to particles that had not been reacted with peptides to allow quantification of the attached fluorophore-peptide absorbance (fluorescein peak absorbance=495 nm; extinction coefficient=$72,000\times10^6$ $cm^-M^{-1}$). NP concentration was assessed by recording its absorbance at 400 nm with an extinction coefficient of $2.07\times10^6$ $cm^{-1}$ $M^{-1}$, Comparison of these concentrations allowed quantitation of the average peptide-to-NP ratios. All samples were normalized to 5 µM based on peptide concentration and stored in 4° C.

In Vitro Screen of Extracellular Protease Activations on Nanoparticle Pro-Diagnostic reagents The 43 normalized (based on 5 µM peptide concentrations) pP-NPs were aliquoted on a clear half-96-well plate. From the aliquoted "stock" plate, 20 µL of each sample was taken out and put into a black half-area 96-well plate. MMP-2 was dissolved in 1×HEPES salt buffer (with 5 mM $CaCl_2$)) at 64 nM, and the solution was heated at 37° C. for 15 minutes to activate the enzyme. 20 µL of the MMP-2 solution was put into each of all 43 wells (which already contained the pP-NP samples) on the black half-96-well plate such that each well had 32 nM MMP-2 and 2.5 µM peptide concentrations. The plate was read immediately and every 1-min following for 90 min by using a microplate fluorimeter (Molecular Devices Corporation; Gemini EM; excitation: 485 nm, emission: 538 nm, cutoff: 530 nm) to sense the cleaved fluorophore signals. The protease activities for particular peptide substrate were measured by the fluorophore intensity levels over time. The basic physical concept is that when the peptide-fluorophore was attached to the NP iron core, the fluorescence of the fluorophore is quenched by the neighboring absorption iron cores. However, when the peptide were cleaved (now de-quench from iron core), an increase in fluorescence can be detected as it diffuses away from the particle core. Same steps were repeated for MMP-7, MMP-8, MMP-9, and MMP-14.

Other proteases (Thrombin, factor Xa, tissue factor, and Cathepsin B) dissolved in 1×HEPES (but no $CaCl_2$)) were used to test the enzyme activities at a final concentration of 32 nM. 20 µL Dulbecco's Modified Eagle Medium (DMEM, GibcoBRL, Rockville, Md.) with 10% fetal bovine serum was put into each well of the prepared black half-96-well plate as well. The DMEM with 10% serum served as the control for the experiment. The initial slope of time over fluorophore intensity level ($V_0$=milli-unit per minute) was plotted for each trials from each samples. There were total of 43 samples and 10 proteases (MMP-2, MMP-7, MMP-8, MMP-9, MMP-14, thrombin, factor Xa, tissue factor, Cathepsin B, and DMEM with 10% serum). The data were then collected and analyzed, and the around 10 most effective samples were selected for future in vivo experiment.

HT-1080/MDA-MB-435 cancer cell culture and implantation

HT-1080 human fibrosarcoma cells (American Type Culture Collection; ATCC) were cultured in tissue culture flasks (150 $cm^2$) by using cell media solution consist of DMEM (89%), fetal bovine serum (10%; Invitrogen), and penicillin/streptomycin (1%). The cells were grown over several generation (n=4-5) and were then concentrated to around 2×$10^6$ million cells/mL in a serum-free solution (66% DMEM, 33% matrix gel, and 1% penicillin/streptomycin). 200 µL of cell solution were injected subcutaneously into each of the nude mice (Nu/Nu; strain code: 088; Charles River Laboratories, Inc., Wilmington, Mass.). For each mouse, 100 µL of the cell solution were injected into each of the nude mouse on the regions of upper right/left thigh (thus, 200 µL total per mouse) below the skin but not into the tissues. The cells would gradually settled and started growing into a sizable tumor (diameter=1 cm) in around 14 days. MDA-MB-435 was processed in the exact same way as HT-1080 with one exception: the injection solution contained 50% 2×$10^6$ million cells/mL and 50% DMEM.

Circulation Assessment of Nanoparticle Pro-Diagnostic Reagents In Vivo

Thrombin-specific pP-NPs samples (2 n-mol based on peptide concentration) were injected into each of four 1-month old adult female white mice (Swiss Webster; strain code: 024; Charles River Laboratories, Inc., Wilmington, Mass.). The reagents (also referred to herein as NP-chaperones) were allowed to circulate in the bloodstream for 5 min (the endpoint of which was defined as 0 hr). 15 µL of blood samples were taken retro-orbitally with heparinized capillary tubes at the following time points: 0 hr, 1 hr, 3 hr, 6 hr, 8 hr, and 12 hr. 10 µL of the blood sample was mixed gently with 40 µL 1×PBS containing 10 mM EDTA to chelate blood calcium and prevent coagulation; the mixture was vortexed and centrifuged to pellet the red blood cells which were then discarded. 30 µL of the supernatant (blood plasma) was put into a well on a 24-by-36-microarray plate.

The intensity of the NP-linked Vivotag-750 fluorescence in the blood plasma sample was detected with the Odyssey imaging system (Westburg, Leusden, Netherlands). All fluorescence intensity levels were normalized to the 0 hr time point (defined as 100%). Bi-exponential lines of best fit were drawn for all samples to calculate the half-life points.

In Vivo Assessment of Tumor and Clotting-Factor Protease Activity

Out of the nine selected peptide-PEG-NP (pP-NPs), the first seven peptide were targeted for tumor monitoring while last two peptide were chosen for internal, vascular injury assessment. These nine pP-NPs were re-synthesized in larger quantity (at least 100 n-moles based on peptide concentrations). Each of the nine pP-NPs (around 5 n-moles) was reacted with VT-750 flourophore (at five-fold molar excess to the peptide concentrations on the NPs) for 2 hr, and the excess un-reactive VT-750 were filtered out to <0.01% by spinning down on 100 k filter column. The VT-750 was now covalently connected to the end of the peptides on pP-NPs, and we abbreviate these products as 750-pP-NPs.

The two thrombin-specific-cleavage 750-pP-NP chaperones were each taken out based on 1-nmol VT-750 concentrations, combined together, and re-suspended to 200 uL of 1×PBS. After fed on non-flourophore diet for >1 wk, 9 nude mice were each injected intravenously with the 200 uL of the 750-pP-NPs; immediately, 4 of the 9 mice were slightly injured on both thigh muscles while 1 of the 9 was injured on only one thigh muscles. All mice were imaged for the bio-distribution of NP chaperones in vivo (Odyssey imaging systems; Westburg, Leusden, Netherlands) by tracing VT-750 for 2-hr period with 10-min intervals. The bio-distributions of 750-pP-NPs over time in each mouse were quantified (ImageJ; NIH), and the organs of interest included bladder, kidney, liver, and spleen. The seven MMP-specific cleavage 750-pP-NP chaperones were each taken out based on 0.3-nmol VT-750 concentrations, combined together, and re-suspended to 200 uL of 1×PBS. After fed on non-flourophore diet for >1 wk, 9 nude mice (3 with HT-1080 tumors, 3 with MDA-MB-435 tumors, and 3 with no tumor) were each injected intravenously with the 200 uL of the 750-pP-NPs. The bio-distribution of 750-pP-NPs over time in each mouse were traced and quantified for 2-hr-period with 10-min intervals. If the NP chaperones have been stored in the fridge for more than 6 hr, it is suggested to spin them down in 100 k filter column in a volume 20-fold of the original samples to get rid of the free peptides and/or VT-750.

The remaining pP-NPs from the nine selected samples were grouped into seven MMP-specific pP-NPs (MMP:pP-NPs) and two thrombin-specific pP-NPs (thrombin:pP-NPs); the pP-NPs in each group were present in the same amount based on peptide concentrations. 2 n-mol of MMP:pP-NPs (based on peptide concentrations) was injected into each of the 16 nude mice (4 with HT-1080 tumors, 4 with MDA-MB-435 tumors, 4 with no tumor but injury, and 4 with no tumors and no injury); the urine of all 12 mice were collected after 2 hr of injections. 2 n-mol of thrombin:pP-NPs were injected into 8 Swiss Webster mice (immediately after injection, 4 were slightly injured on both thigh muscles) and 4 nude mice with MDA-MB-435 tumors; the urine of all 12 mice were collected after 1 hr of injections. In addition, 2 n-mol of a free thrombin peptide was injected into each of the 8 mice, and 4 were immediately injured afterward; the urine samples of all 8 mice were collected after 1 hr of injections. In the waiting periods between the injections of the NP chaperones and the excretions of the urine, all mice were anesthetized with isoflurane (2-chloro-2-(difluoromethoxy)-1,1,1-trifluoro-ethane). After urine excretions for each mouse, each urine sample volume was diluted to 500 uL by adding $ddH_2O$. 100 µL of each 500 uL urine sample was put into a well on a black half-96-well plate, and a microplate fluorimeter (Molecular Devices Corporation; Gemini EM; excitation: 485 nm, emission: 538 nm, cutoff: 530 nm) was use to measure the relative fluorophore units (RFU) of each sample. Furthermore, 100 µL of each 250 uL urine sample was analyzed on HPLC-MS-MS for specific peptide sequences injected into the mice.

Statistical Analysis

Since that the sample sizes for both the nude mice and the white mice were very small and that a normal distribution could not be assumed, a Student two-tailed t-test was performed for all statistical tests in this study. The null hypothesis was that the two groups (e.g. tumor vs. non-tumor; injured vs. non-injured) do not differ in the amount of peptides excreted, and p-value <0.05 would reject the null hypothesis.

Figure 1B:
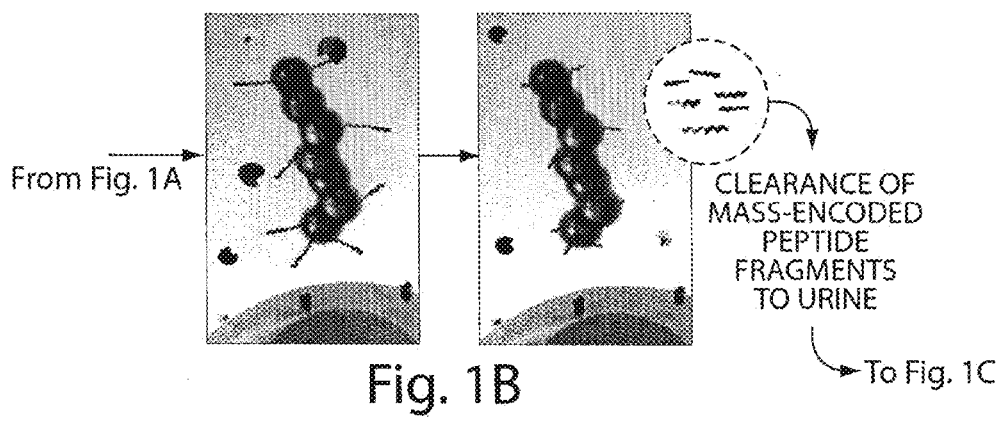
Figure 1C:
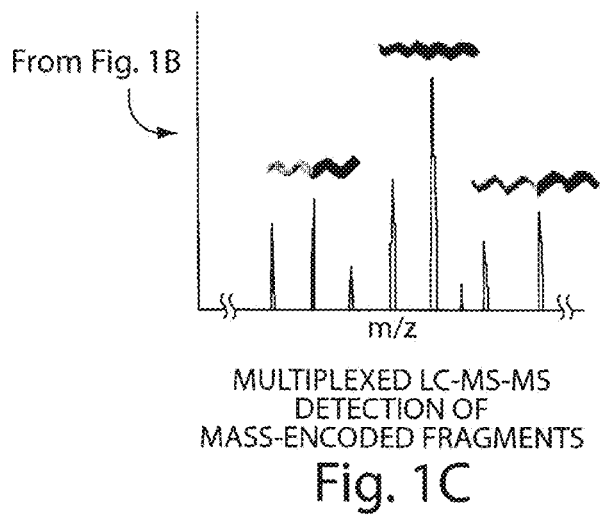

Example 2: Preparation of Pro-Diagnostic Reagents 43 pro-diagnostic reagents composed of peptide-PEG-nanoparticles (pP-NPs) were prepared and analyzed with a spectrometer to assess the number of peptides bound to each nanoparticle. The reagents were designed to enable rapid high throughput screening methods. FIG. 1 is a schematic depicting a method according to the invention for multiplexed in vivo enzyme profiling of mass-coded nanoparticle based pro-diagnostic reagents.

Example 3: In Vitro Screen of Extracellular Protease Activations on Pro-Diagnostic Reagents Initially, we established that the pro-diagnostic reagents could target tumors or injuries. We then conducted a screen of 43 pro-diagnostic reagents to fluorescently find optimal sequences for detection of tumor and injury proteases. The protease activities for a particular peptide substrate were measured by the fluorophore intensity levels over time. When the peptide-fluorophore (signature molecule) was attached to the nanoparticle iron core (carrier), the fluorescence of the fluorophore was quenched by the neighboring absorption iron cores. However, when the peptides were cleaved, the fluorophores were no longer quenched and, an increase in fluorescence was detected.

Figure 3A:
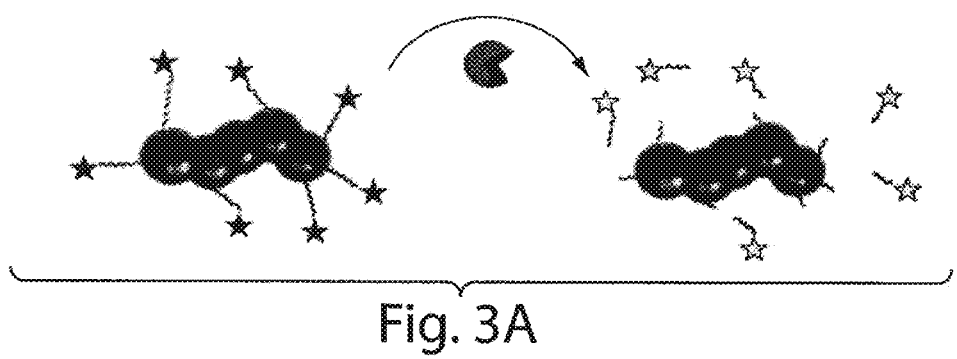
FIG. 3A is a schematic of the pro-diagnostic reagent, with the circles referring to the carrier, the star is a signature molecule, and the zigzag line refers to the enzyme susceptible domain.
Figure 3B:
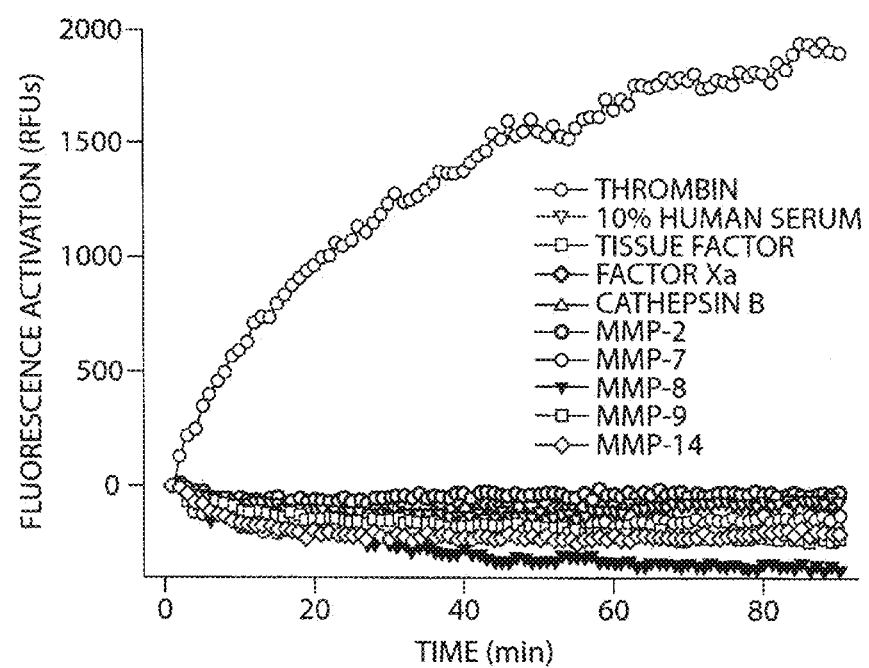
FIG. 3B is a graph depicting fluorescence activation versus time.
Figure 3C:
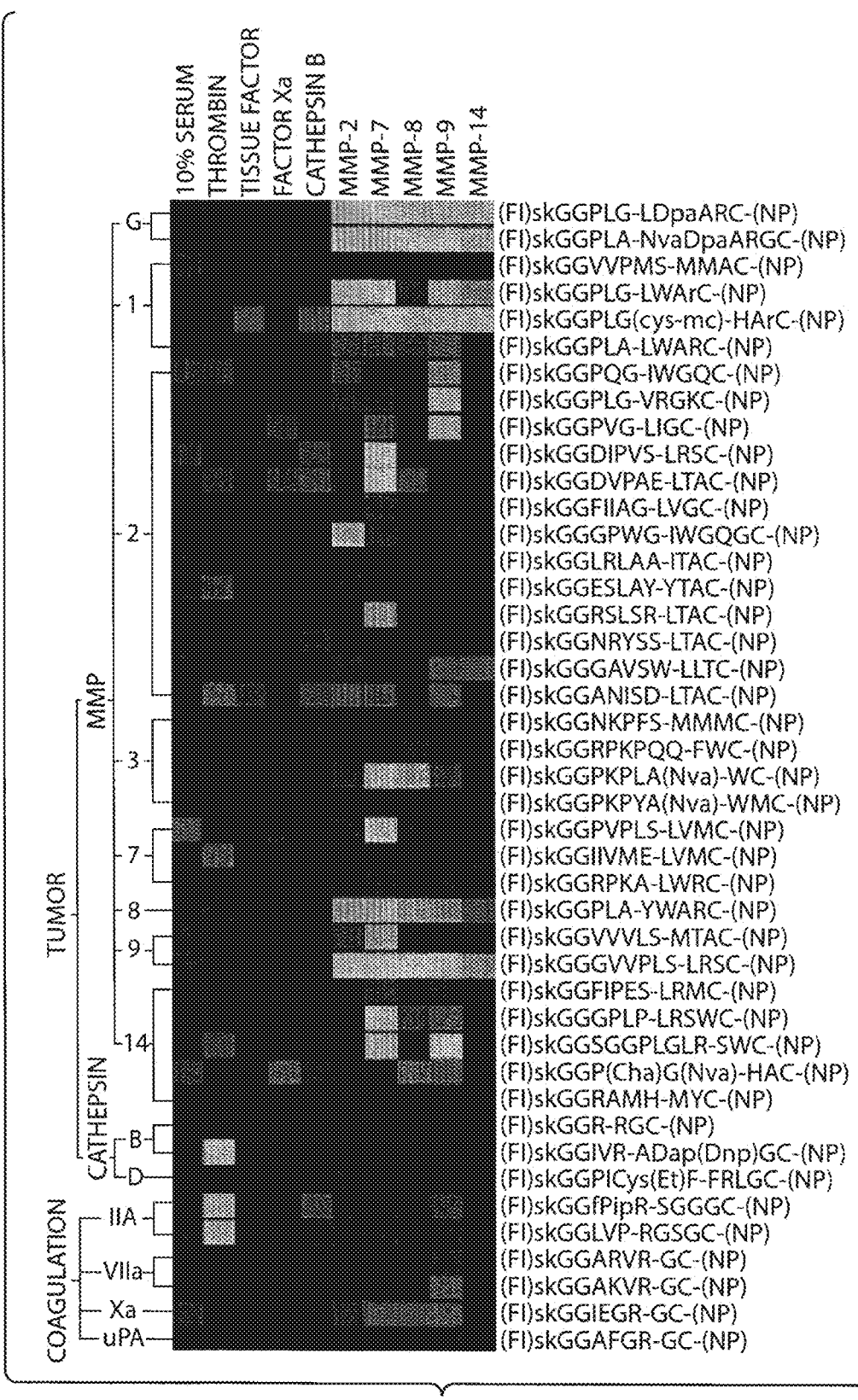
FIG. 3C depicts data on 43 pro-diagnostic reagents (with enzyme susceptible domains listed to the right for detection of tumor and injury enzymes.

FIG. 3A is a schematic of the pro-diagnostic reagent, with the circles referring to the carrier, the star is a signature molecule, and the zigzag line refers to the enzyme susceptible domain. FIG. 3B is a graph depicting fluorescence activation versus time. FIG. 3C depicts data on 43 pro-diagnostic reagents (with enzyme susceptible domains listed to the right for detection of tumor and injury enzymes.

FIG. 4 is a Table depicting the mass detection of ejected fragments in vitro. The results confirmed that the fluorescent results from the screen could also be detected by analyzing the mass of ejected fragments in vitro.

Example 4: Tumor and Wound Targeting with Pro-Diagnostic Reagents

Figure 2A:
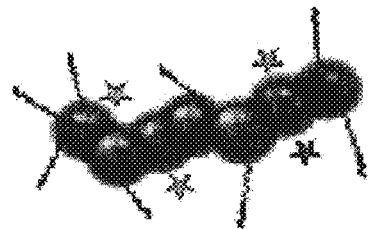
FIGS. 2A-2E show data depicting the process of tumor and wound targeting with pro-diagnostic reagents.
Figure 2B:
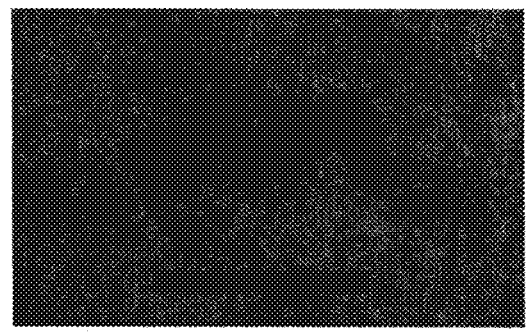
Figure 2C:
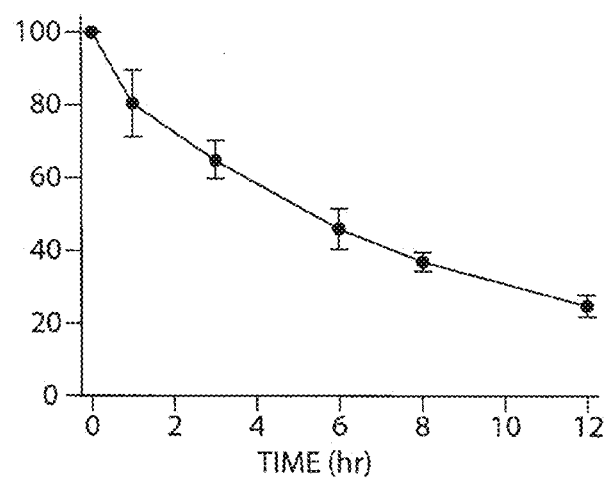
Figure 2D:
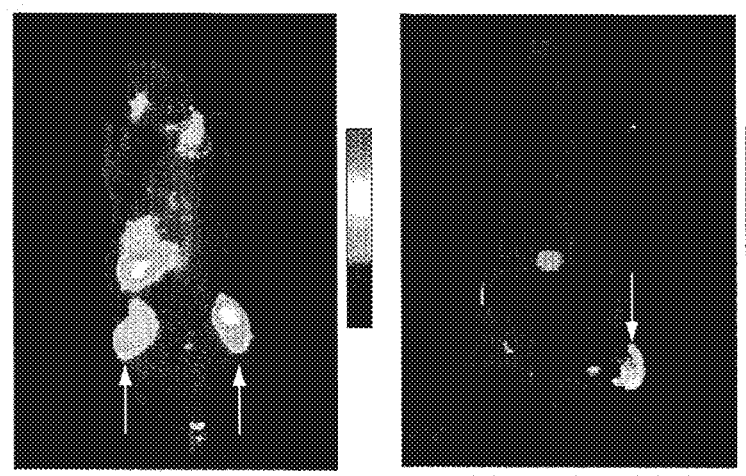
Figure 2E:
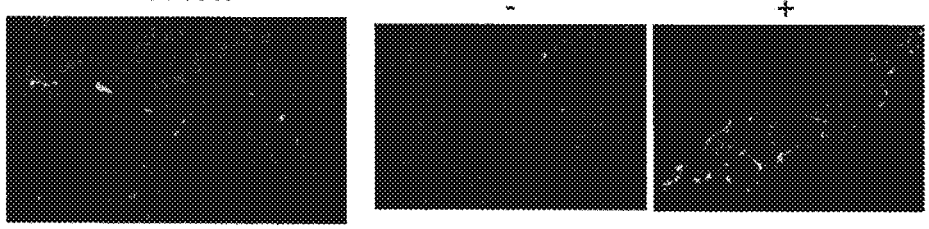

Tumor and wound targeting with pro-diagnostic reagents shows how the carriers enhance the circulation time of the peptides (which would otherwise clear within minutes) and enable targeting to either tumors or injuries. FIG. 2 shows data depicting the process of tumor and wound targeting with pro-diagnostic reagents. FIG. 2A is a schematic of the pro-diagnostic reagent, with the circles referring to the carrier, the star is a fluorescent molecule, and the zigzag line refers to the enzyme susceptible domain and the signature molecule (darker end region). FIG. 2B is an electron micrograph of the pro-diagnostic reagent. FIG. 2C is a graph depicting the circulation time of the pro-diagnostic reagent, by plotting detection of the carrier in the blood with respect to time after intravenous injection. FIG. 2D is photographs of mice having either tumors or injuries (left and right panels, respectively) administered the pro-diagnostic reagent. FIG. 2E is histopathological analysis of carrier homing to tumors or regions of injury.

Example 5: In Vivo Assessment of Tumor and Clotting-Factor Protease Activity

Figure 5A:
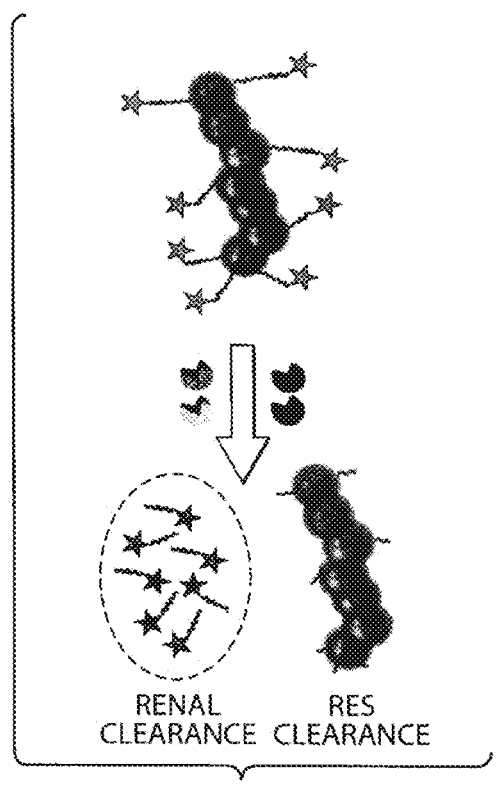
FIGS. 5A-5C depict the results of fluorescent detection of urinary reporter activation by tumors and injuries in vivo.
Figure 5B:
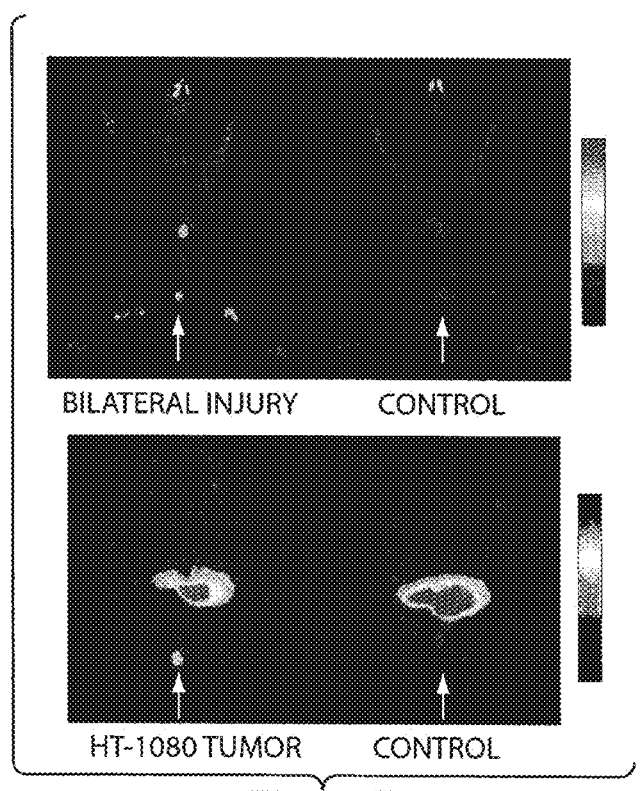
Figure 5C:
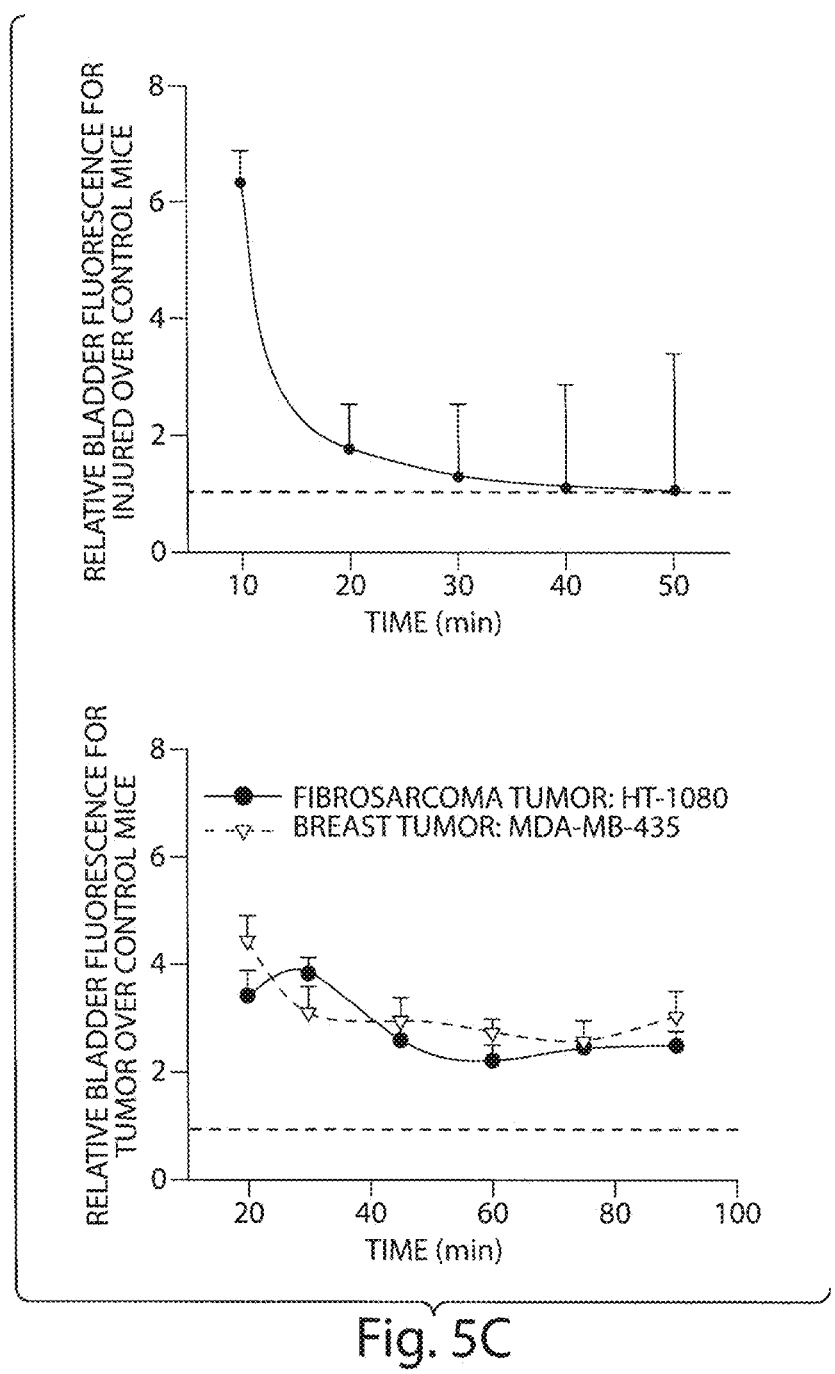

The circulation time of pro-diagnostic reagents in vivo was assessed. Optimized pro-diagnostic reagents were injected intravenously into mice and the cleaved peptide (signature component) was fluorescently tracked into the urine after injection. The intensity of the fluorescence in the blood plasma sample was detected with the Odyssey imaging system. FIG. 5 depicts the results of fluorescent detection of urinary reporter activation by tumors and injuries in vivo. FIG. 5A is a schematic of the pro-diagnostic reagent as shown in FIG. 3A, further depicting the portion of the molecule that undergoes renal clearance and the portion that undergoes RES clearance. FIG. 5B is a set of photographs of that were intravenously administered the optimized pro-diagnostic reagent for injury detection (top) or tumor detection (bottom). Half the mice that were administered the optimized pro-diagnostic agents for injury-detection suffered bilateral hind limb injuries (left side of the photograph) while the control mice had no injuries (right side of the photograph). Half the mice administered the optimized pro-diagnostic agents for tumor-detection harbored human fibrosarcoma tumors (HT-1080) (left side of photograph), while the other mice contained no tumors (right side of photograph). FIG. 5C is a set of graphs depicting relative bladder fluorescence for tumor (bottom panel) or injured (top panel) versus control mice in order to track the entrance of cleaved signature peptide into the urine after injection. Bi-exponential lines of best fit were drawn for all samples to calculate the half-life points.

Figure 6A:
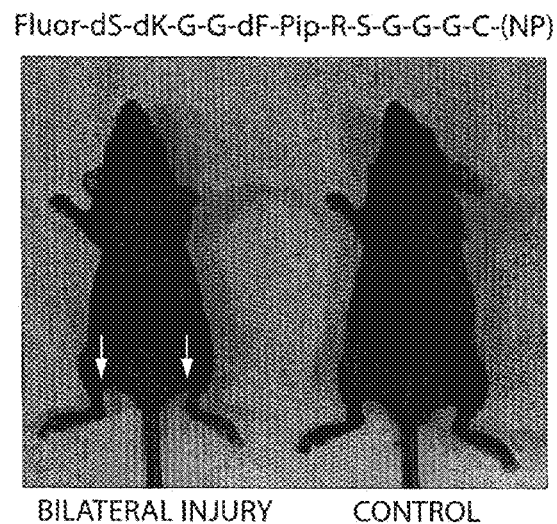
FIGS. 6A-6B show LC/MS quantitation of signature molecules in urine.
Figure 6B:
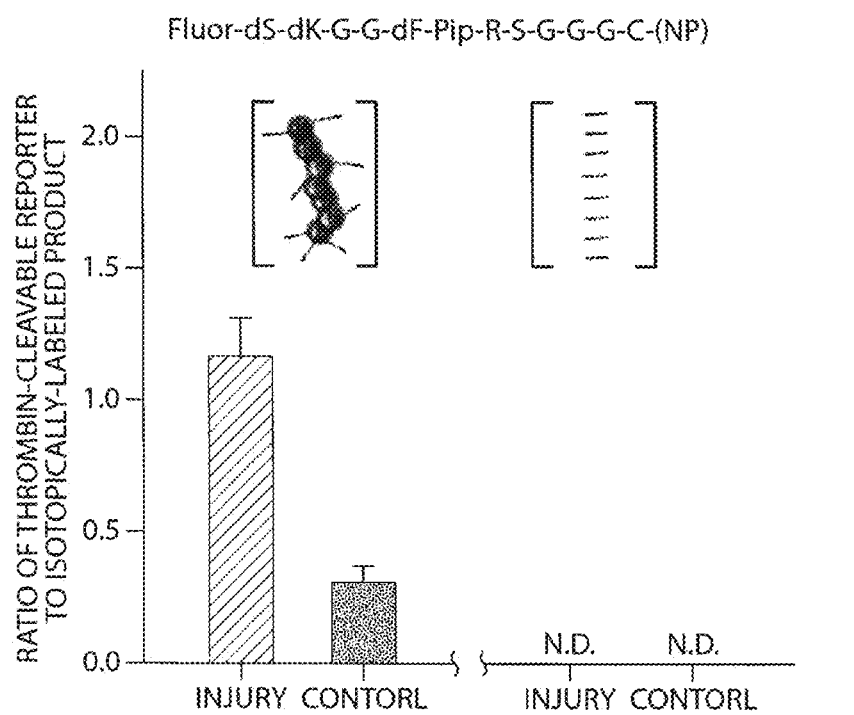

FIG. 6 shows LC/MS quantitation of signature molecules in urine. FIG. 6A is a photograph of an experimental mouse, having bilateral injury and a control uninjured mouse. FIG. 6B is a graph depicting the ratio of signature molecule (from thrombin cleavable proteolytic susceptible domain) to isotopically labeled product in injured versus control mice.

Example 6: In Vitro Assessment of an Implantable Diagnostic Capsule

Figure 7A:
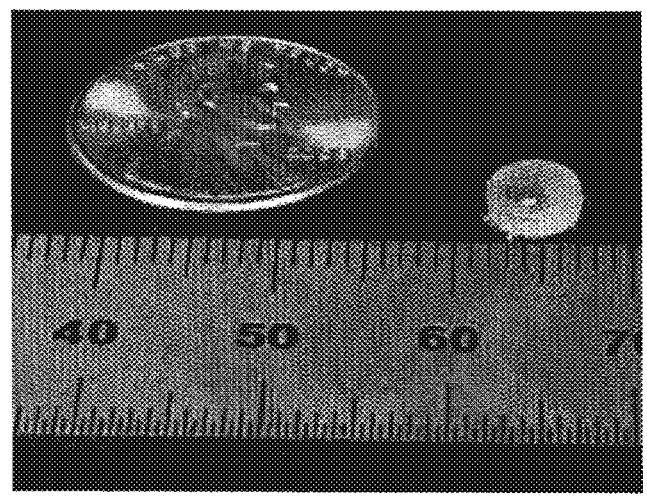
FIG. 7A shows a photograph of a typical implantable capsule in comparison to a penny and a ruler.
Figure 7B:
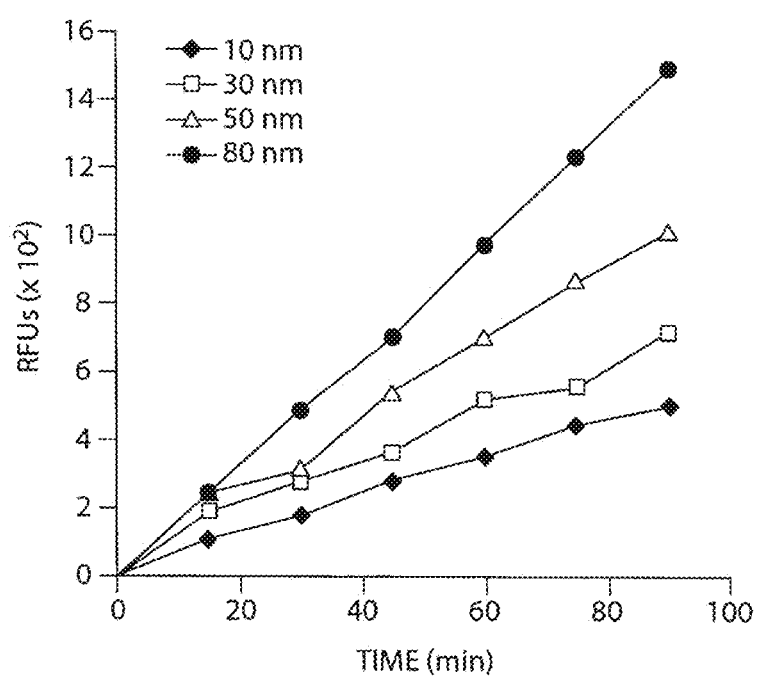
FIG. 7B is a graph showing measurements of thrombin-cleaved peptide efflux from implantable diagnostic capsules sealed with semi-permeable membranes of different pore sizes. Capsules made with membranes of pore size 10, 30, 50 or 80 nm were loaded with nanoparticles functionalized with GGdFPipRSGGGC (SEQ ID NO: 8) and exposed to solutions of thrombin or factor Xa (a cognate and a non-cognate protease, respectively). Thrombin-specific cleavage was monitored over time and is shown in terms of kinetics of reporter release.

FIG. 7 shows an exemplary embodiment of an implantable diagnostic capsule. FIG. 7A shows a photograph of a typical implantable capsule as described, for example, in Daniel, K. D., et al., *Implantable diagnostic device for cancer monitoring*. Biosensors and Bioelectronics 24 (2009) 3252-3257 which can be used according to the invention for loading nanoparticles. Nanoparticles can be loaded into the well-shaped reservoir and sealed by a semi-permeable polycarbonate membrane enabling free traffic of enzymes and other molecules but limiting the extracapsule diffusion of nanoparticles. FIG. 7B shows measurements of thrombin-cleaved peptide efflux from implantable diagnostic capsules sealed with semi-permeable membranes of different pore sizes. Capsules made with membranes of pore size 10, 30, 50 or 80 nm were loaded with nanoparticles functionalized with GGdFPipRSGGGC (SEQ ID NO: 8) and exposed to solutions of thrombin or factor Xa (a cognate and a non-cognate protease, respectively). Thrombin-specific cleavage was monitored over time by measuring extra capsule fluorescence every 30 minutes, normalizing over factor Xa. The kinetics of reporter release is shown.

Example 7: Optimization of Peptide Reporters for LC/MS Detection

A series of peptides (A1-A14) of different sequence were investigated to determine optimal sequence length and charge density that would enable facile detection via LC/MS. Three representative proteolytic products, sequences GGVVVLS (SEQ ID NO: 19), GGPVG (SEQ ID NO: 13), and GGdFPipR (SEQ ID NO: 17) were selected and appended with peptide caps of differing length and charge density (FIG. 8A). The sequences were then detected via LC/MS. FIG. 8B shows normalized relative intensities of the peptide reporters. The inset of FIG. 8B shows a magnification of the normalized relative intensities of the peptide sequences A1-A6 as measured via LC/MS. In general, hydrophilic sequences appended with shorter caps were more readily detected. For example, peptides A5 and A6, containing the shortest caps of the group of peptides containing the proteolytic product GGVVVLS (SEQ ID NO: 19), were more readily detected than other peptides of that group, which contained longer, or less hydrophilic caps. A hydrophilic molecule is a molecule that can transiently hydrogen-bond with water and is, thus, soluble in water and, in some embodiments, in other polar solvents. Hydrophilicity of peptides can be modulated according to methods well known in the art. In some embodiments, removal of the fluorescein tag will increase the hydrophilicity of the peptides reported in this disclosure. In some embodiments, modification of the sequences to contain positively charged residues (Histidine, Lysine, and Arginine) and/or negatively charged residues (glutamic acid and aspartic acid) will increase the hydrophilicity. Similarly, peptides A11 and A12, containing the shortest caps of the group of peptides containing the proteolytic product GGPVG (SEQ ID NO: 13), were more readily detected than other peptides of that group, which contained longer, or less hydrophilic caps. Of the tested cap sequences Fl-dR-dS-dR (SEQ ID NO: 20) and Fl-dR-G-dS-dR (SEQ ID NO: 21) were determined to be advantageous. Accordingly, for non-fluorescent detection, the cap sequences dR-dS-dR (SEQ ID NO: 35) and dR-G-dS-dR (SEQ ID NO: 36) were determined to be advantageous. Using the results from the optimization experiments as guidelines, a revised list of pro-diagnostic peptides were designed for optimal LC/MS detection. The following pro-diagnostic peptides optimized for LC/MS detection were designed:

Example 8: In Vitro Multiplexed Analysis of Protease Activity by LC/MS

Figure 9A:
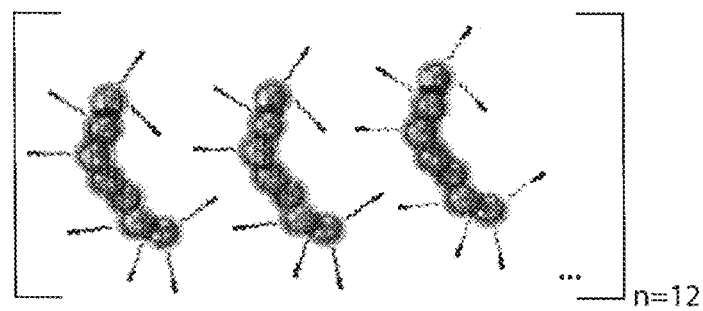
FIG. 9A is a schematic of the pro-diagnostic reagent, showing two identical cocktails of 12 pro-diagnostic nanoparticles, each functionalized with a different peptide, with the circles referring to the carrier, the star is a signature molecule, and the zigzag line refers to the enzyme susceptible domain.
Figure 9B:
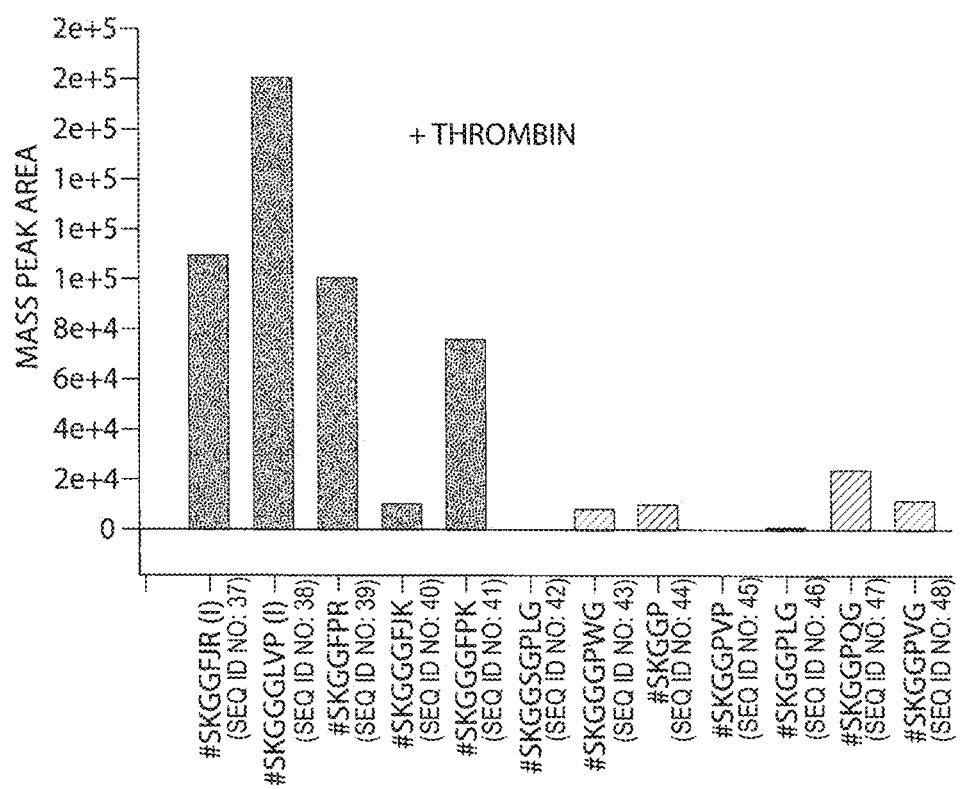
FIG. 9B is a graph depicting LC/MS peak area measurements of all twelve peptides after exposure of the first multiplex cocktail to thrombin. Left to right the sequences on the X-axis correspond to SEQ ID NOs. 37-48.
Figure 9C:
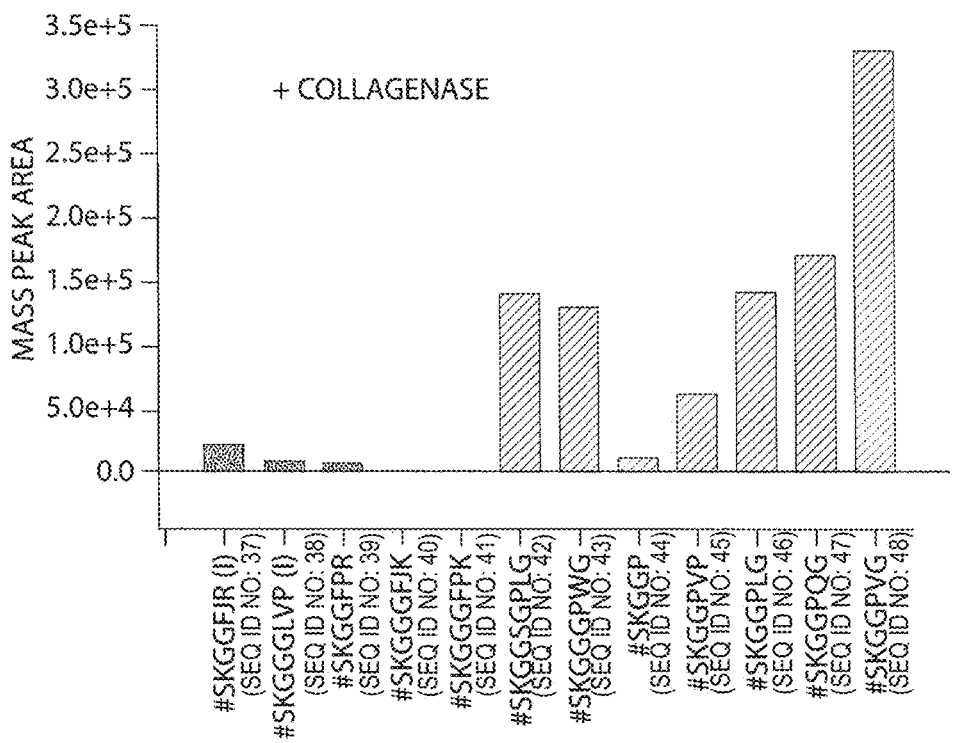
FIG. 9C is a graph depicting LC/MS peak area measurements of all twelve peptides after exposure of the second multiplex cocktail to collagenase. Left to right the sequences on the X-axis correspond to SEQ ID NOs. 37-48.
Figure 9D:
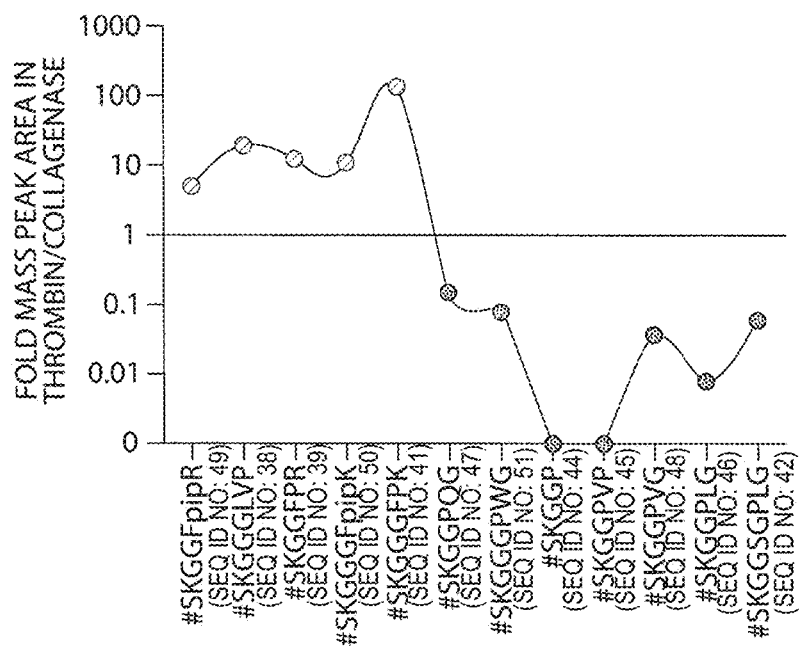
FIG. 9D is a graph showing the ratio of the LC/MS peak area for each peptide reporter after exposure to thrombin over the peak area measured after exposure to collagenase. Left to right the sequences on the X-axis correspond to SEQ ID NOs. 49, 38, 39, 50, 41, 47, 51, 44, 45, 48, 46, and 42.

Two identical cocktails of 12 pro-diagnostic nanoparticles, each functionalized with a different peptide (FIG. 9A), were exposed to thrombin or collagenase and the proteolytically released reporters were analyzed by LC/MS. Six of the peptides contained target peptide sequences for thrombin, whereas the other six peptides contained target peptide sequences for collagenase. LC/MS peak area measurements of all twelve peptides after exposure of the first multiplex cocktail to thrombin and after exposure of the second multiplex cocktail to collagenase are shown in FIG. 9B and FIG. 9C, respectively. In the cocktail exposed to thrombin, peptide reporters cleaved from peptides containing a thrombin target site (left six bars) were predominantly detected over peptide reporters cleaved from peptides containing a collagenase target site (right six bars), as shown in FIG. 9B. In the cocktail exposed to collagenase, peptide reporters cleaved from peptides containing a collagenase target site (right six bars) were predominantly detected over peptide reporters cleaved from peptides containing a thrombin target site (left six bars), as shown in FIG. 9C. FIG. 9 D shows the ratio of the LC/MS peak area for each peptide reporter after exposure to thrombin over the peak area measured after exposure to collagenase.

The foregoing written specification is considered to be sufficient to enable one skilled in the art to practice the invention. The present invention is not limited in scope by the examples provided, since the examples are intended as illustrations of various aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

| Peptide | Sequence | |
|---|---|---|
| A | Fl-dR-dS-dR-G-G-P-Q-G-I-W-G-Q-C | (SEQ ID NO: 22) |
| B | Fl-dR-G-dS-dR-G-G-P-L-G-V-R-G-K-C | (SEQ ID NO: 23) |
| C | Fl-dR-G-dS-dR-G-G-P-L-A-Nva-Dpa-A-R-G-C | (SEQ ID NO: 24) |
| D | Fl-dR-G-dS-dR-G-G-P-V-G-L-I-G-C | (SEQ ID NO: 25) |
| E | Fl-dR-dS-dR-G-G-P-V-P-L-S-L-V-M-C | (SEQ ID NO: 26) |
| F | Fl-dR-G-dS-dR-G-G-V-V-V-L-S-M-T-A-C | (SEQ ID NO: 27) |
| G | Fl-dR-G-dS-dR-G-G-S-G-G-P-L-G-L-R-S-W-C | (SEQ ID NO: 28) |
| H | Fl-dR-G-dS-dR-G-G-P-W-G-I-W-G-Q-G-C | (SEQ ID NO: 29) |
| I | Fl-dR-G-G-dS-G-G-dF-Pip-R-S-G-G-G-C | (SEQ ID NO: 30) |
| J | Fl-dR-dS-dR-G-G-L-V-P-R-G-S-G-C | (SEQ ID NO: 31) |
| Ia | Fl-dR-G-G-dS-G-G-F-P-R-S-G-G-G-C | (SEQ ID NO: 32) |
| Ib | Fl-dR-G-G-dS-G-G-G-dF-Pip-K-S-G-G-G-C | (SEQ ID NO: 33) |
| Ic | Fl-dR-G-G-dS-G-G-G-dF-P-K-S-G-G-G-C | (SEQ ID NO: 34) |

The invention claimed is:

1. A reagent comprising
a carrier domain, wherein the carrier domain is a particle and is greater than 5 nm in size;
an enzyme susceptible domain linked to the carrier domain; and,
a signature molecule linked to the enzyme susceptible domain, wherein the signature molecule comprises a peptide or nucleic acid and is optimized for LC/MS detection.

2. An implantable device housing a structure comprising a carrier domain linked to a signature producing agent that is capable of modifying a biological substrate to produce a signature molecule.

3. The implantable device of claim 2, wherein the signature producing agent is an enzyme.

4. The implantable device of claim 3, wherein the enzyme is a protease or a glycosidase.

5. The implantable device of claim 2, wherein the implantable device is an implantable capsule with a semipermeable membrane that encapsulates the structure.

6. The implantable device of claim 2, wherein the implantable device is a chip having the structure attached thereto.

7. The implantable device of claim 2, wherein the implantable device is a sustained-release formulation.

8. The reagent of claim 1, wherein the enzyme susceptible domain is a peptide, a nucleotide, or a carbohydrate.

9. The reagent of claim 1, wherein the enzyme susceptible domain is a peptide and the peptide comprises GGPQGIWGQC (SEQ ID NO: 1), GGPLGVRGKC (SEQ ID NO: 2), GGPLANvaDpaARGC (SEQ ID NO: 3), GGPVGLIGL (SEQ ID NO: 4), GGPVPLSLVMC (SEQ ID NO: 5), GGSGGPLGLRSWC (SEQ ID NO: 6), GGGPWGIWGQGC (SEQ ID NO: 7), GGdFPipRSGGGC (SEQ ID NO: 8), or GGLVPRGSGC (SEQ ID NO: 9).

10. The reagent of claim 1, wherein the signature molecule further comprises a small molecule, fluorophore, quencher, carbohydrate, and/or particle.

11. The reagent of claim 1, wherein the signature molecule comprises a peptide.

12. The reagent of claim 11, wherein the peptide is GGPQG (SEQ ID NO: 10), GGPLG (SEQ ID NO: 11), GGPLA (SEQ ID NO: 12), GGPVG (SEQ ID NO: 13), GGPVPLS (SEQ ID NO: 14), GGSGGPLG (SEQ ID NO: 15), GGGPWG (SEQ ID NO: 16), GGdFPipR (SEQ ID NO: 17), or GGLVP (SEQ ID NO: 18).

13. The reagent of claim 1, wherein the signature molecule comprises a peptide comprising two basic amino acid residues.

14. The reagent of claim 13, wherein the two basic amino acid residues are dR residues.

15. The reagent of claim 13, wherein the two basic amino acid residues are separated by at least one non-basic amino acid residue.

16. The reagent of claim 13, wherein the signature molecule comprises at least three but not more than five amino acid residues.

17. The reagent of claim 13, wherein the signature molecule is hydrophilic.

18. The reagent of claim 13, wherein the signature molecule comprises SEQ ID NOs: 20, 21, 35, or 36.

19. The reagent of claim 1, wherein the carrier domain is a polymer based microparticle, an iron oxide microparticle, or nanoparticle, an inorganic carrier, an organic carrier, a small molecule, a peptide, a nucleic acid, or a carbohydrate.

20. The reagent of claim 1, wherein the carrier domain comprises a RGD peptide.

21. The reagent of claim 1, wherein the carrier domain comprises an antibody.

22. The reagent of claim 1, wherein the carrier domain includes a targeting domain.

23. The reagent of claim 1, wherein the carrier domain is a therapeutic agent.

24. The reagent of claim 1, wherein the carrier domain further comprises a therapeutic agent incorporated into a particle carrier.

25. A reagent comprising
a carrier domain having a plurality of enzyme susceptible domains linked to the carrier domain wherein each enzyme susceptible domain is linked to a non-fluorescent signature molecule.

26. A composition comprising
a plurality of pro-diagnostic reagents comprising a carrier domain, an enzyme susceptible domain linked to the carrier domain; and, a non-fluorescent signature molecule linked to the enzyme susceptible domain.

27. The reagent of claim 25, wherein the non-fluorescent signature molecule comprises a peptide, nucleic acid, small molecule, carbohydrate, and/or particle.

28. The reagent of claim 25, wherein the non-fluorescent signature molecule is optimized for LC/MS detection.

29. The composition of claim 26, wherein the non-fluorescent signature molecule comprises a peptide, nucleic acid, small molecule, carbohydrate, and/or particle.

30. The composition of claim 26, wherein the non-fluorescent signature molecule is optimized for LC/MS detection.

* * * * *

SEQUENCE LISTING

<160> NUMBER OF SEQ ID NOS: 51

<210> SEQ ID NO 1
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 1

Gly Gly Pro Gln Gly Ile Trp Gly Gln Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Gly Gly Pro Leu Gly Val Arg Gly Lys Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa is Norvaline (Nva)
<220> FEATURE:
<221> NAME/KEY: misc_feature
<222> LOCATION: (7)..(7)
<223> OTHER INFORMATION: Xaa is N - beta - (2,4 - dinitrophenyl) (Dap)

<400> SEQUENCE: 3

Gly Gly Pro Leu Ala Xaa Xaa Ala Arg Gly Cys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Gly Gly Pro Val Gly Leu Ile Gly Leu
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 5

Gly Gly Pro Val Pro Leu Ser Leu Val Met Cys
1               5                   10

```
<210> SEQ ID NO 6
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 6

Gly Gly Ser Gly Gly Pro Leu Gly Leu Arg Ser Trp Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 7

Gly Gly Gly Pro Trp Gly Ile Trp Gly Gln Gly Cys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: D-isomer
<220> FEATURE:
<221> NAME/KEY: misc_feature
<222> LOCATION: (4)..(4)
<223> OTHER INFORMATION: Xaa is pipecolic acid (Pip)

<400> SEQUENCE: 8

Gly Gly Phe Xaa Arg Ser Gly Gly Gly Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 9

Gly Gly Leu Val Pro Arg Gly Ser Gly Cys
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 10

Gly Gly Pro Gln Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic polypeptide
```

```
<400> SEQUENCE: 11

Gly Gly Pro Leu Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 12

Gly Gly Pro Leu Ala
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 13

Gly Gly Pro Val Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 14

Gly Gly Pro Val Pro Leu Ser
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 15

Gly Gly Ser Gly Gly Pro Leu Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 16

Gly Gly Gly Pro Trp Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic polypeptide
```

```
<220> FEATURE:
<221> NAME/KEY: misc_feature
<222> LOCATION: (3)..(3)
<223> OTHER INFORMATION: D-isomer
<220> FEATURE:
<221> NAME/KEY: misc_feature
<222> LOCATION: (4)..(4)
<223> OTHER INFORMATION: Xaa is Pipecolic acid (Pip)

<400> SEQUENCE: 17

Gly Gly Phe Xaa Arg
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 18

Gly Gly Leu Val Pro
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 19

Gly Gly Val Val Val Leu Ser
1               5

<210> SEQ ID NO 20
<211> LENGTH: 3
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(3)
<223> OTHER INFORMATION: D-isomer

<400> SEQUENCE: 20

Arg Ser Arg
1

<210> SEQ ID NO 21
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
```

```
<220> FEATURE:
<221> NAME/KEY: misc_feature
<222> LOCATION: (3)..(4)
<223> OTHER INFORMATION: D-isomer

<400> SEQUENCE: 21

Arg Gly Ser Arg
1

<210> SEQ ID NO 22
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(3)
<223> OTHER INFORMATION: D-isomer

<400> SEQUENCE: 22

Arg Ser Arg Gly Gly Pro Gln Gly Ile Trp Gly Gln Cys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (3)..(4)
<223> OTHER INFORMATION: D-isomer

<400> SEQUENCE: 23

Arg Gly Ser Arg Gly Gly Pro Leu Gly Val Arg Gly Lys Cys
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (3)..(4)
<223> OTHER INFORMATION: D-isomer
<220> FEATURE:
<221> NAME/KEY: misc_feature
<222> LOCATION: (10)..(10)
<223> OTHER INFORMATION: Xaa is Norvaline (Nva)
```

```
<220> FEATURE:
<221> NAME/KEY: misc_feature
<222> LOCATION: (11)..(11)
<223> OTHER INFORMATION: Xaa is N - beta - (2,4 - dinitrophenyl) (Dap)

<400> SEQUENCE: 24

Arg Gly Ser Arg Gly Gly Pro Leu Ala Xaa Xaa Ala Arg Gly Cys
1               5                   10                  15

<210> SEQ ID NO 25
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (3)..(4)
<223> OTHER INFORMATION: D-isomer

<400> SEQUENCE: 25

Arg Gly Ser Arg Gly Gly Pro Val Gly Leu Ile Gly Cys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(3)
<223> OTHER INFORMATION: D-isomer

<400> SEQUENCE: 26

Arg Ser Arg Gly Gly Pro Val Pro Leu Ser Leu Val Met Cys
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (3)..(4)
<223> OTHER INFORMATION: D-isomer
```

```
<400> SEQUENCE: 27

Arg Gly Ser Arg Gly Gly Val Val Val Leu Ser Met Thr Ala Cys
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (3)..(4)
<223> OTHER INFORMATION: D-isomer

<400> SEQUENCE: 28

Arg Gly Ser Arg Gly Gly Ser Gly Gly Pro Leu Gly Leu Arg Ser Trp
1               5                   10                  15

Cys

<210> SEQ ID NO 29
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (3)..(4)
<223> OTHER INFORMATION: D-isomer

<400> SEQUENCE: 29

Arg Gly Ser Arg Gly Gly Gly Pro Trp Gly Ile Trp Gly Gln Gly Cys
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (4)..(4)
<223> OTHER INFORMATION: D-isomer
```

```
<220> FEATURE:
<221> NAME/KEY: misc_feature
<222> LOCATION: (7)..(7)
<223> OTHER INFORMATION: D-isomer
<220> FEATURE:
<221> NAME/KEY: misc_feature
<222> LOCATION: (8)..(8)
<223> OTHER INFORMATION: Xaa is pipecolic acid (Pip)

<400> SEQUENCE: 30

Arg Gly Gly Ser Gly Gly Phe Xaa Arg Ser Gly Gly Gly Cys
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(3)
<223> OTHER INFORMATION: D-isomer

<400> SEQUENCE: 31

Arg Ser Arg Gly Gly Leu Val Pro Arg Gly Ser Gly Cys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (4)..(4)
<223> OTHER INFORMATION: D-isomer

<400> SEQUENCE: 32

Arg Gly Gly Ser Gly Gly Phe Pro Arg Ser Gly Gly Gly Cys
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (4)..(4)
<223> OTHER INFORMATION: D-isomer
```

```
<220> FEATURE:
<221> NAME/KEY: misc_feature
<222> LOCATION: (8)..(8)
<223> OTHER INFORMATION: D-isomer
<220> FEATURE:
<221> NAME/KEY: misc_feature
<222> LOCATION: (9)..(9)
<223> OTHER INFORMATION: Xaa is pipecolic acid (Pip)

<400> SEQUENCE: 33

Arg Gly Gly Ser Gly Gly Gly Phe Xaa Lys Ser Gly Gly Gly Cys
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: N-terminal Fluorescein
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (4)..(4)
<223> OTHER INFORMATION: D-isomer
<220> FEATURE:
<221> NAME/KEY: misc_feature
<222> LOCATION: (8)..(8)
<223> OTHER INFORMATION: D-isomer

<400> SEQUENCE: 34

Arg Gly Gly Ser Gly Gly Gly Phe Pro Lys Ser Gly Gly Gly Cys
1               5                   10                  15

<210> SEQ ID NO 35
<211> LENGTH: 3
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(3)
<223> OTHER INFORMATION: D-isomer

<400> SEQUENCE: 35

Arg Ser Arg
1

<210> SEQ ID NO 36
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: D-isomer
<220> FEATURE:
<221> NAME/KEY: misc_feature
<222> LOCATION: (3)..(4)
<223> OTHER INFORMATION: D-isomer
```

```
<400> SEQUENCE: 36

Arg Gly Ser Arg
1

<210> SEQ ID NO 37
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: X may be Leucine or Isoleucine

<400> SEQUENCE: 37

Ser Lys Gly Gly Phe Xaa Arg
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 38

Ser Lys Gly Gly Gly Leu Val Pro
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 39

Ser Lys Gly Gly Phe Pro Arg
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: X may be Leucine or Isoleucine

<400> SEQUENCE: 40

Ser Lys Gly Gly Gly Phe Xaa Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 41

Ser Lys Gly Gly Gly Phe Pro Lys
1               5
```

```
<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 42

Ser Lys Gly Gly Ser Gly Pro Leu Gly
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 43

Ser Lys Gly Gly Gly Pro Trp Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 44

Ser Lys Gly Gly Pro
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 45

Ser Lys Gly Gly Pro Val Pro
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 46

Ser Lys Gly Gly Pro Leu Gly
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 47

Ser Lys Gly Gly Pro Gln Gly
1               5
```

```
<210> SEQ ID NO 48
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 48

Ser Lys Gly Gly Pro Val Gly
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: X is a pipecolic acid

<400> SEQUENCE: 49

Ser Lys Gly Gly Phe Xaa Arg
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: X is a pipecolic acid

<400> SEQUENCE: 50

Ser Lys Gly Gly Gly Phe Xaa Lys
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 51

Ser Lys Gly Gly Gly Pro Trp Gly
1               5
```